US008871237B2

(12) United States Patent
Zussman et al.

(10) Patent No.: US 8,871,237 B2
(45) Date of Patent: Oct. 28, 2014

(54) MEDICAL SCAFFOLD, METHODS OF FABRICATION AND USING THEREOF

(75) Inventors: Eyal Zussman, Haifa (IL); Erella Livne, Haifa (IL); Samer Srouji, Haifa (IL); Shmuel Chervinsky, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1055 days.

(21) Appl. No.: 11/887,768

(22) PCT Filed: Apr. 4, 2006

(86) PCT No.: PCT/IL2006/000421
§ 371 (c)(1),
(2), (4) Date: Oct. 3, 2007

(87) PCT Pub. No.: WO2006/106506
PCT Pub. Date: Oct. 12, 2006

(65) Prior Publication Data
US 2009/0074832 A1    Mar. 19, 2009

Related U.S. Application Data

(60) Provisional application No. 60/667,666, filed on Apr. 4, 2005.

(51) Int. Cl.
| | | |
|---|---|---|
| A61F 13/00 | (2006.01) | |
| A61F 2/00 | (2006.01) | |
| A61L 27/56 | (2006.01) | |
| D01D 5/00 | (2006.01) | |
| A61L 27/38 | (2006.01) | |
| A61L 27/50 | (2006.01) | |

(52) U.S. Cl.
CPC ............ *A61L 27/3821* (2013.01); *A61L 27/56* (2013.01); *D01D 5/0007* (2013.01); *A61L 27/50* (2013.01); *A61L 27/3847* (2013.01); *A61L 27/3895* (2013.01)
USPC ...................................................... 424/423

(58) Field of Classification Search
CPC . A61L 27/56; A61L 27/3821; A61L 27/3847; A61L 27/3895; A61L 27/50; D01D 5/0007
USPC .......................................... 424/400, 422, 423
See application file for complete search history.

(56) References Cited

U.S. PATENT DOCUMENTS

| | | | |
|---|---|---|---|
| 2003/0100944 A1* | 5/2003 | Laksin et al. ................ | 623/1.44 |
| 2008/0160856 A1* | 7/2008 | Chen et al. .................... | 442/341 |

FOREIGN PATENT DOCUMENTS

WO    WO 02/49536    6/2002

OTHER PUBLICATIONS

Communication Relating to the Results of the Partial International Search Dated Apr. 10, 2007 From the International Searching Authority Re.: Application No. PCT/IL2006/000421.
International Preliminary Report on Patentability Dated Oct. 18, 2007 From the International Bureau of WIPO Re.: Application No. PCT/IL2006/000421.
International Search Report and the Written Opinion Dated May 24, 2007 From the International Searching Authority Re.: Application No. PCT/IL2006/000421.
Communication Pursuant to Article 94(3) EPC Dated Apr. 3, 2008 From the European Patent Office Re.: Application No. 06728224.4.
Response Dated Sep. 5, 2010 to Office Action of Mar. 4, 2010 From the Israel Patent Office Re.: Application No. 186241.
Khil et al. "Novel Fabricated Matrix Via Electrospinning for Tissue Engineering", Journal of Biomedical Materials Research, Part B: Applied Biomaterials, 72(B): 117-124, 2005. p. 117, l-h col., Paragraph 1—p. 118, l-h col., Paragraph 2, p. 121, r-h col., Paragraph 3—p. 123, l-h col., Paragraph 1.
Office Action Dated Mar. 4, 2010 From the Israel Patent Office Re.: Application No. 186241 and Its Translation Into English.
Office Action Dated Oct. 5, 2011 From the Israel Patent Office Re.: Application No. 186241 and Its Translation Into English.
Office Action Dated Apr. 1, 2012 From the Israel Patent Office Re.: Application No. 186241 and Its Translation Into English.
Communication Pursuant to Article 94(3) EPC Dated Aug. 2, 2013 From the European Patent Office Re.: Application No. 06728224.4.

* cited by examiner

*Primary Examiner* — Ruth Davis

(57) ABSTRACT

Articles of manufacturing comprising electrospun elements having continuous or stepwise gradients of porosity, average pore size, weight per volume and/or of agents for promoting cell colonization, differentiation, extravasation and/or migration are provided. Also provided are methods of manufacturing and using same for guiding tissue regeneration.

38 Claims, 6 Drawing Sheets
(4 of 6 Drawing Sheet(s) Filed in Color)

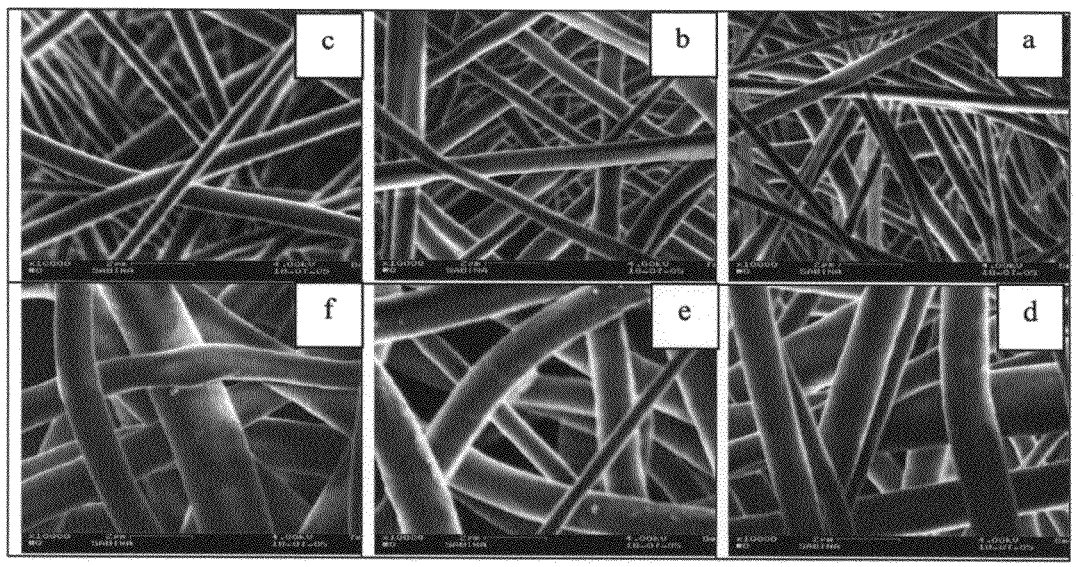
Figs. 6a-f

US 8,871,237 B2

MEDICAL SCAFFOLD, METHODS OF FABRICATION AND USING THEREOF

RELATED APPLICATIONS

This Application is a National Phase of PCT Patent Application No. PCT/IL2006/000421 having International Filing Date of Apr. 4, 2006, which claims the benefit of U.S. Provisional Patent Application No. 60/667,666 filed on Apr. 4, 2005. The contents of the above Applications are all incorporated herein by reference.

FIELD AND BACKGROUND OF THE INVENTION

The present invention relates to electrospun elements having a continuous or stepwise gradient of porosity, average pore size, weight-per-volume and/or agents attached to, embedded or impregnated therein which can be used as medical membranes and scaffolds for guided tissue regeneration, repair and/or implant.

Tissue regeneration, repair and/or implant are used in treating damaged, traumatized, abnormal functioning, diseased and/or dysfunction tissues. Tissue repair and/or regeneration are based on transplanting scaffolds, membranes or matrices along with cells which are capable of growing into and repairing damaged or diseased tissues. Desired scaffolds, membranes or matrices for tissue regeneration are biocompatible and/or biodegradable materials capable of supporting the growth and/or regeneration of soft or hard tissues. Such substances should therefore be compatible with the desired cure.

Due to their wide acceptance as safe and efficient substances, homologous or heterologous tissue-derived materials such as Collagen, fibronectin, chitosan and alginate are conventionally used for tissue regeneration. However, the use of tissue-derived materials can lead to undesirable immunological rejections, blood coagulation and/or tissue hypertrophy.

On the other hand, artificial tissue made of alloplastic, non-degradable synthetic polymers such as polyethylene glycol (PEG), Hydroxyapatite/polycaprolactone (HA/PCL), polyglycolic acid (PGA), Poly-L-lactic acid (PLLA), Poly lactic co glycolide (PLGA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and non biodegradable polytetrafluoroethylene (PTFE) poly-anhydrides, poly-phosphazenes, poly-tetrafluoroethylene (PTFE), and PMMA/polyhydroxyethylmethacrylate (PHEMA) display excellent physical properties including the precise control over the material mechanical properties. However, such synthetic scaffolds lack sufficient bioaffinity and compatibility, homeostatic regulation and many specific cell interactions which regulate cell proliferation and organization.

To overcome such limitations, various hormones, growth factors and extracellular matrix components were either impregnated, mixed or cross-linked to the scaffold backbone. However, such modifications failed sometimes to provide sufficient biological signals which guide cell growth and differentiation.

Bone repair is one of the major challenges for orthopedic medicine. Bone and teeth are molecular composites of inorganic hydroxyapatite and collagen which are arranged in a three-dimensional matrix. Thus, common materials used for hard tissue repair are based on biocompatible ceramics formed on matrix surface having high strength (e.g., a metal matrix), native polymers and/or extracellular matrix proteins, such as Collagen. Collagens, comprise a majority of proteins in connective tissue such as skin, bone, cartilage and tendons.

Biodegradable polymers such as polycaprolacton (PCL), polylactic acid (PLA), polyglycolic acid (PGA), their blends and copolymers exhibit high molecular weight structures which, following hydrolysis or other biologically derived processes, can be break down to less complicated, smaller and soluble molecules. Such degradation can occur under the action of living organisms (e.g., bacteria) or by the various processes in the body, including biochemical and non-enzymatic chemical degradation.

Biodegradable hydrogel scaffolds made of various biodegradable polymers (e.g., collagen based hydrogel) were found suitable for growth and differentiation of bone marrow derived mesenchymal stem cells (MSCs). In addition, enhanced bone defect repair was achieved in hydrogel scaffolds impregnated with growth factors. Other PCL-based polymers or copolymers scaffolds were reported to provide biocompatible structures for both osteogenesis (Yoshimoto et al. 2003) and chondrogenesis (Li et al., 2003; 2005; Tuli et al., 2004). However, although hydrogel scaffolds are biodegradable and capable of promoting cell differentiation in vitro, their relatively small porosity and low strength prevent their use in clinical applications such as bone repair.

Recently, Collagen, PLLA, PLGA, PCL, their blends and copolymers scaffolds were fabricated using electro-spinning (see for example, U.S. Pat. Appl. No. 20040037813 to Simpson David G, et al; Lee Y H, et al., 2005, Biomaterials. 26: 3165-72; Khil M S, et al., 2005, J. Biomed. Mater. Res. B Appl Biomater. 72: 117-24; Li et al., 2002; Yoshimoto et al., 2003). Electro-spinning is a process that uses an electrostatic field to control the formation and deposition of polymers. This process is remarkably efficient, rapid, and inexpensive. In electro-spinning, a polymer solution or melt is charged with an electrostatic potential to create a charge imbalance and then is injected through a needle of a syringe to a grounded target. At a critical voltage, the charge repulsion begins to overcome the surface tension of the polymer drop, extruding an electrically charged jet. The jet within the electrostatic field is directed towards the grounded target, during which time the solvent evaporates and fibers are formed. Electro-spinning produces a single continuous nano to microfibrous filament which is collected by the grounded target as a non-woven fabric (Theron A, et al., 2001). Notably, it is possible to fabricate filaments on the nanometer scale using this technique for in-vivo guided tissue regeneration and or repair. However, the presently available electrospun scaffolds are not suitable for in vivo guided tissue regeneration and/or repair.

SUMMARY OF THE INVENTION

While reducing the present invention to practice, the present inventors have uncovered a method of manufacturing an electrospun element having a continuous or stepwise gradient of porosity, average pore size, weight-per-volume and/or agents attached to, embedded or impregnated therein. Such an electrospun element can be used as a scaffold and/or membrane for guided tissue regeneration and/or repair.

According to one aspect of the present invention there is provided an article of manufacturing comprising an electrospun element having a continuous gradient of average pore size along at least a portion thereof.

According to another aspect of the present invention there is provided an article of manufacturing comprising an electrospun element having a continuous gradient of weight-per-volume along at least a portion thereof.

According to yet another aspect of the present invention there is provided an article of manufacturing comprising an electrospun element having a continuous or stepwise gradient of at least one agent along at least a portion thereof.

According to still another aspect of the present invention there is provided an article of manufacturing comprising an electrospun element having a first surface and a second surface defining a volume therebetween, wherein an average pore size close to the first surface is selected so as to allow migration of at least one population of cells therethrough into the volume, and an average pore size close to the second surface is selected so as to restrict migration of at least one population of cells therethrough into the volume.

According to an additional aspect of the present invention there is provided an article of manufacturing comprising an electrospun element having a gradient of average pore size along at least a portion thereof, the electrospun element being perforated so as to allow selective migration of cells through the electrospun element.

According to yet an additional aspect of the present invention there is provided a method of manufacturing an electrospun element, the method comprising: (a) dispensing from a dispenser at least one liquefied polymer within an electrostatic field in a direction of a rotating collector so as to form at least one jet of polymer fibers; (b) while collecting the at least one jet of polymer fibers on the rotating collector, monotonically varying at least one parameter so as to form an electrospun element characterized by a continuous porosity gradient.

According to still an additional aspect of the present invention there is provided a method of perforating an electrospun element comprising passing an electrical spark through the electrospun element to thereby obtain a perforated electrospun element.

According to a further aspect of the present invention there is provided a method of perforating an electrospun element comprising passing a heated puncturing element through at least a portion of the electrospun element to thereby obtain a perforated electrospun element.

According to yet a further aspect of the present invention there is provided a scaffold comprising an electrospun element consisting of PCL and PLA polymers and/or copolymers, whereby when seeded with bone marrow derived stem cells in an osteoblast differentiation inducing medium containing at least one mineral the scaffold is populated with osteoblasts and mineralizes so as to transform into a mineralized scaffold.

According to still a further aspect of the present invention there is provided a method of inducing ex vivo formation of a tissue, the method comprising: (i) providing a scaffold having an electrospun element having a continuous gradient of average pore size along at least a portion thereof; and (ii) seeding the scaffold with cells in a medium selected suitable for proliferation, differentiation and/or migration of the cells to thereby induce the formation of the tissue.

According to still a further aspect of the present invention there is provided a method of inducing ex vivo formation of a tissue, the method comprising: (i) providing a scaffold having an electrospun element having a continuous porosity gradient along at least a portion thereof; and (ii) seeding the scaffold with cells in a medium selected suitable for proliferation, differentiation and/or migration of the cells to thereby induce the formation of the tissue.

According to still a further aspect of the present invention there is provided a method of inducing ex vivo formation of a tissue, the method comprising: (i) providing a scaffold having an electrospun element having a continuous gradient of weight per volume along at least a portion thereof; and (ii) seeding the scaffold with cells in a medium selected suitable for proliferation, differentiation and/or migration of the cells to thereby induce the formation of the tissue.

According to still a further aspect of the present invention there is provided a method of inducing ex vivo formation of a tissue, the method comprising: (i) providing a scaffold having an electrospun element having a continuous gradient of at least one agent; and (ii) seeding the scaffold with cells in a medium selected suitable for proliferation, differentiation and/or migration of the cells to thereby induce the formation of the tissue.

According to still a further aspect of the present invention there is provided a method of inducing in vivo formation of a tissue, the method comprising: (i) providing a scaffold having an electrospun element having a continuous gradient of at least one agent; and (ii) implanting the scaffold in a subject to thereby induce the formation of the tissue.

According to still a further aspect of the present invention there is provided a method of inducing in vivo formation of a tissue, the method comprising: (i) providing a scaffold having an electrospun element having a continuous gradient of average pore size along at least a portion thereof; and (ii) implanting the scaffold in a subject to thereby induce the formation of the tissue.

According to still a further aspect of the present invention there is provided a method of inducing in vivo formation of a tissue, the method comprising: (i) providing a scaffold having an electrospun element having a continuous porosity gradient along at least a portion thereof; and (ii) implanting the scaffold in a subject to thereby induce the formation of the tissue.

According to still a further aspect of the present invention there is provided a method of inducing in vivo formation of a tissue, the method comprising: (i) providing a scaffold having an electrospun element having a continuous gradient of weight-per-volume along at least a portion thereof; and (ii) implanting the scaffold in a subject to thereby induce the formation of the tissue.

According to still a further aspect of the present invention there is provided a method of treating a subject having a pathology characterized by a tissue damage or loss, the method comprising: (i) providing a scaffold having an electrospun element having a continuous gradient of weight-per-volume along at least a portion thereof; and (ii) implanting the scaffold in a subject to thereby induce the formation of the tissue, thereby treating the subject.

According to still a further aspect of the present invention there is provided a method of treating a subject having a pathology characterized by a tissue damage or loss, the method comprising: (i) providing a scaffold having an electrospun element having a continuous gradient of at least one agent; and (ii) implanting the scaffold in a subject to thereby induce the formation of the tissue, thereby treating the subject.

According to still a further aspect of the present invention there is provided a method of treating a subject having a pathology characterized by a tissue damage or loss, the method comprising: (i) providing a scaffold having an electrospun element having a continuous gradient of average pore size along at least a portion thereof; and (ii) implanting the scaffold in a subject to thereby induce the formation of the tissue, thereby treating the subject.

According to still a further aspect of the present invention there is provided a method of treating a subject having a pathology characterized by a tissue damage or loss, the method comprising: (i) providing a scaffold having an electrospun element having a continuous porosity gradient along at least a portion thereof; and (ii) implanting the scaffold in a subject to thereby induce the formation of the tissue, thereby treating the subject.

According to still a further aspect of the present invention there is provided an article of manufacturing comprising an electrospun element having a continuous porosity gradient along at least a portion thereof.

According to further features in preferred embodiments of the invention described below, the method further comprising: (c) varying a concentration of at least one agent attached to and/or embedded in said at least one liquefied polymer and/or impregnated in at least a portion of said polymer fibers so as to form an electrospun element characterized by a continuous or stepwise gradient of said at least one agent along at least a portion thereof.

According to still further features in the described preferred embodiments the article of manufacturing further comprises a culture medium for promoting proliferation of at least one population of cells being in contact with the electrospun element.

According to still further features in the described preferred embodiments the continuous gradient of average pore size is selected so as to allow migration of at least one population of cells through one side of the electrospun element.

According to still further features in the described preferred embodiments the continuous gradient of average pore size is selected so as to restrict migration of at least one population of cells through a second side, the second side opposite the first side, of the electrospun element.

According to still further features in the described preferred embodiments the at least one population of cells are selected capable of guiding tissue regeneration.

According to still further features in the described preferred embodiments the at least one population of cells are osteoblast cells.

According to still further features in the described preferred embodiments the at least one population of cells are endothelial cells.

According to still further features in the described preferred embodiments the at least one population of cells for which the migration is restricted are fibroblast cells.

According to still further features in the described preferred embodiments the culture medium includes a mineralizing agent.

According to still further features in the described preferred embodiments the continuous gradient of average pore size has a maximal average pore diameter of about 200 μm and a minimal average pore diameter of about 0.1 μm According to still further features in the described preferred embodiments the article of manufacturing further comprises an electrospun element having a stepwise gradient of average pore size along at least a portion thereof.

According to still further features in the described preferred embodiments the electrospun element exhibits a porosity gradient along at least a portion thereof.

According to still further features in the described preferred embodiments the porosity gradient is a continuous porosity gradient.

According to still further features in the described preferred embodiments the continuous porosity gradient has a maximal porosity of about 95% and a minimal porosity of about 50%.

According to still further features in the described preferred embodiments the continuous porosity gradient has a maximal porosity of about 90% and a minimal porosity of about 50%.

According to still further features in the described preferred embodiments the continuous porosity gradient has a maximal porosity of about 85% and a minimal porosity of about 50%.

According to still further features in the described preferred embodiments the porosity gradient is a stepwise porosity gradient.

According to still further features in the described preferred embodiments the electrospun element comprises at least one fiber.

According to still further features in the described preferred embodiments at least a portion of the at least one fiber is hollow.

According to still further features in the described preferred embodiments at least a portion of the at least one fiber comprises a core shell structure.

According to still further features in the described preferred embodiments an average diameter of the at least one fiber is characterized by a variance of about 10%.

According to still further features in the described preferred embodiments an average diameter of the at least one fiber is characterized by a variance of less than about 10%.

According to still further features in the described preferred embodiments the at least one fiber exhibit a gradient of average diameter along at least a portion of the electrospun element.

According to still further features in the described preferred embodiments the gradient of average diameter is a continuous gradient.

According to still further features in the described preferred embodiments the gradient of average diameter is a stepwise gradient.

According to still further features in the described preferred embodiments the electrospun element has a gradient of weight-per-volume along at least a portion thereof.

According to still further features in the described preferred embodiments the gradient of weight-per-volume is a continuous gradient.

According to still further features in the described preferred embodiments the gradient of weight-per-volume is a stepwise gradient.

According to still further features in the described preferred embodiments the electrospun element comprises at least one biocompatible polymer.

According to still further features in the described preferred embodiments the at least one biocompatible polymer is selected from the group consisting of PCL, Calcium sulfate, PLA, PGA, PEG, Collagen, PEG-DMA; Alginate, Hydroxyapatite and Chitosan.

According to still further features in the described preferred embodiments the at least one biocompatible polymer comprises at least two biocompatible polymers.

According to still further features in the described preferred embodiments the at least two biocompatible polymers are selected from the group consisting of PCL, Calcium sulfate, PLA, PGA, PEG, Collagen, PEG-DMA, Alginate, Hydroxyapatite and Chitosan.

According to still further features in the described preferred embodiments the electrospun element comprises a mixture of the at least two biocompatible polymers.

According to still further features in the described preferred embodiments the electrospun element comprises a co-polymer.

According to still further features in the described preferred embodiments the co-polymer comprising at least one biocompatible polymer.

According to still further features in the described preferred embodiments the electrospun element comprises at least one biodegradable polymer.

According to still further features in the described preferred embodiments the at least two biocompatible polymers are biodegradable.

According to still further features in the described preferred embodiments the article of manufacturing further comprises at least one agent.

According to still further features in the described preferred embodiments the at least one agent is for promoting cell colonization, differentiation, extravasation and/or migration.

According to still further features in the described preferred embodiments the at least one agent is an amino acid, peptide, a polypeptide, a protein, a DNA, an RNA, a lipid and/or a proteoglycan.

According to still further features in the described preferred embodiments the protein is selected from the group consisting of an extracellular matrix protein, a cell adhesion protein, a growth factor, a cytokine, a protease and a protease substrate.

According to still further features in the described preferred embodiments the at least one agent is attached to, embedded in or impregnated in at least a portion of the electrospun element.

According to still further features in the described preferred embodiments the extracellular matrix protein is selected from the group consisting of fibrinogen, Collagen, fibronectin, vimentin, microtubule-associated protein 1D, Neurite outgrowth factor (NOF), bacterial cellulose (BC), laminin and gelatin.

According to still further features in the described preferred embodiments the cell adhesion protein is selected from the group consisting of integrin, proteoglycan, glycosaminoglycan, laminin, intercellular adhesion molecule (ICAM) 1, N-CAM, cadherin, tenascin, gicerin, RGD peptide, and nerve injury induced protein 2 (ninjurin2).

According to still further features in the described preferred embodiments the growth factor is selected from the group consisting of epidermal growth factor, transforming growth factor-$\alpha$, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-$\beta$, vascular endothelial growth factor, angiopeptin and platelet-derived growth factor.

According to still further features in the described preferred embodiments the protease protein is selected from the group consisting of pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2.

According to still further features in the described preferred embodiments the continuous gradient of weight-per-volume is selected so as to allow migration of at least one population of cells through one side of the electrospun element.

According to still further features in the described preferred embodiments the continuous gradient of weight-per-volume is selected so as to restrict migration of at least one population of cells through a second side of the electrospun element.

According to still further features in the described preferred embodiments the at least one parameter is selected from the group consisting of an angular velocity of the rotating collector, a strength of the electrostatic field, a directionality of the electrostatic field, a distance between the dispenser and the rotating collector, a size of a dispensing hole of the dispenser, numbers of the dispensers and a dispensing rate of the at least one liquefied polymer.

According to still further features in the described preferred embodiments the liquefied polymer is a soluble polymer.

According to still further features in the described preferred embodiments the liquefied polymer comprises at least one biocompatible polymer.

According to still further features in the described preferred embodiments the at least one liquefied polymer comprises a co-polymer.

According to still further features in the described preferred embodiments the at least one liquefied polymer comprises at least one agent.

According to still further features in the described preferred embodiments the method further comprises perforating the electrospun element.

According to still further features in the described preferred embodiments perforating is effected using a laser beam.

According to still further features in the described preferred embodiments perforating is effected using an electrical spark.

According to still further features in the described preferred embodiments perforating is effected using a mechanical perforation.

According to still further features in the described preferred embodiments the mechanical perforation is effected using a heated puncturing element.

According to still further features in the described preferred embodiments the heated puncturing element is heated at a temperature of at least 90° C.

According to still further features in the described preferred embodiments the electrical spark is provided at a voltage of at least 20 kV.

According to still further features in the described preferred embodiments the electrical spark is provided at a voltage in the range of 10-40 kV.

According to still further features in the described preferred embodiments the voltage is provided for a time period of about 1 second per hole.

According to still further features in the described preferred embodiments the electrical spark is provided at a distance of about 10 mm.

According to still further features in the described preferred embodiments the puncturing element is heated to a temperature of at least 90° C.

According to still further features in the described preferred embodiments the puncturing element is heated to a temperature of about 100° C.

According to still further features in the described preferred embodiments passing is effected for a time range of 1-30 seconds.

According to still further features in the described preferred embodiments passing is effected for a time period of about 10 seconds.

According to still further features in the described preferred embodiments the scaffold further comprises a hydrogel.

According to still further features in the described preferred embodiments the hydrogel is formed from a biocompatible polymer.

According to still further features in the described preferred embodiments the electrospun element is characterized by a predetermined average pore size selected so as to restrict migration of fibroblast cells therethrough.

According to still further features in the described preferred embodiments the electrospun element is characterized by a predetermined average pore size selected so as to allow penetration of oxygen molecules therethrough.

According to still further features in the described preferred embodiments the electrospun element is characterized by a predetermined average pore size selected so as to allow penetration of nutrients therethrough.

According to still further features in the described preferred embodiments the electrospun element is characterized by a predetermined average pore diameter having a diameter selected from about 0.1 micrometer to about 200 micrometer.

According to still further features in the described preferred embodiments the electrospun element is characterized by a variance pore size of less than about 20% of the average pore size.

According to still further features in the described preferred embodiments the electrospun element is characterized by a porosity of at least 50%.

According to still further features in the described preferred embodiments the electrospun element forms a membrane.

According to still further features in the described preferred embodiments the electrospun element exhibits a tubular structure.

According to still further features in the described preferred embodiments the hydrogel forms a layer and whereas the layer is positioned over or underneath the electrospun element.

According to still further features in the described preferred embodiments the hydrogel forms a composite structure with the electrospun element.

According to still further features in the described preferred embodiments the PCL and PLA are provided at a weight ratio of at least 1:1, respectively.

According to still further features in the described preferred embodiments the PCL and PLA are provided at a weight ratio of about 1:3, respectively.

According to still further features in the described preferred embodiments the PCL and PLA copolymers are formed at a weight ratio of at least 3:1, respectively According to still further features in the described preferred embodiments the PCL and PLA copolymers are formed at a weight ratio of about 1:3

According to still further features in the described preferred embodiments the scaffold further comprises at least one agent.

According to still further features in the described preferred embodiments the electrospun element further comprises a hydrogel.

According to still further features in the described preferred embodiments the tissue is a bone tissue.

According to still further features in the described preferred embodiments the continuous porosity gradient is selected so as to allow migration of at least one population of cells through one side of the electrospun element.

According to still further features in the described preferred embodiments the continuous porosity gradient is selected so as to restrict migration of at least one population of cells through a second side of the electrospun element.

According to still further features in the described preferred embodiments the scaffold further comprising PGA polymer and/or copolymer.

According to still further features in the described preferred embodiments the cells are stem cells.

The present invention successfully addresses the shortcomings of the presently known configurations by providing an electrospun element having continuous or stepwise gradient of porosity, average pore size and/or weight per volume with or without a continuous or stepwise gradient of at least one agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-f are photomicrographs illustrating the PCL:PLA (3:1 ratio, respectively) electrospun scaffold in the presence (FIGS. 1b-d) or absence (FIG. 1a) of mesenchymal stem cells (MSCs) cultured in a medium containing osteogenic supplements (100 μg/ml ascorbic acid, 10 mM sodium β-glycerophosphate and $10^{-8}$ M dexamethasone; the "osteogenic medium" hereinafter). FIG. 1a—a control PCL:PLA (3:1 ratio) scaffold following 7 days in culture in the absence of MSCs; FIGS. 1b-d—the PCL:PLA (3:1 ratio) scaffold containing MSC derived cells following 7 (FIG. 1b), 14 (FIG. 1c), or 21 (FIG. 1d;) days in culture in the presence of the osteogenic medium; FIGS. 1e and f—Alizarin red S staining of MSC-derived osteogenic cells following 14 (FIG. 1e) or 21 (FIG. 1f) days in culture. Note the presence of MSC-derived osteoprogenitor cells (FIG. 1c) following 14 days in culture and MSC-derived osteogenic cells (FIG. 1d) following 21 days in culture. Also note the deposition of mineralized matrix by the cells following 14 and 21 days as indicated by the red staining using Alizarin red S (FIGS. 1e-f). Scale bars in FIGS. 1a-f=1 mm.

FIGS. 2a-d are scanning electron micrographs (SEM) of the PCL:PLA (3:1 ratio, respectively) electrospun scaffold in the presence (FIGS. 2c-d) or absence (FIGS. 2a-b) of MSCs. Note the 3-D porous structure of the scaffold containing cells adhered to the scaffold fibers (FIGS. 2c and d). Also note the initial deposition of extracellular matrix (ECM) on the non woven scaffold fibers following 7 days in culture in the presence of the osteogenic medium (FIGS. 2c and d). Magnifications: FIG. 2a—×10,000; FIG. 2b—×5,000; FIG. 2c—×5,000; FIG. 2d—×2,000. Scale bars: FIG. 2a=2 μm; FIG. 2b=10 μm; FIG. 2c=5 μm; FIG. 2d=20 μm.

FIGS. 3a-d are SEM micrographs of bone marrow-derived MSCs cultured for 21 days on the PCL:PLA (3:1 ratio, respectively) electrospun scaffold in the presence of the osteogenic medium. Note the dense material between the cells and rigid appearance of mineralized fibers (FIGS. 3a-d). Magnifications: FIG. 3a—×5,000, FIG. 3b—×10,000, FIG. 3c—×5,000, FIG. 3d—×10,000. Scale bars: FIG. 3a=5 μm; FIG. 3b=2 μm; FIG. 3c=20 μm; FIG. 3d=2 μm.

Figure 4:
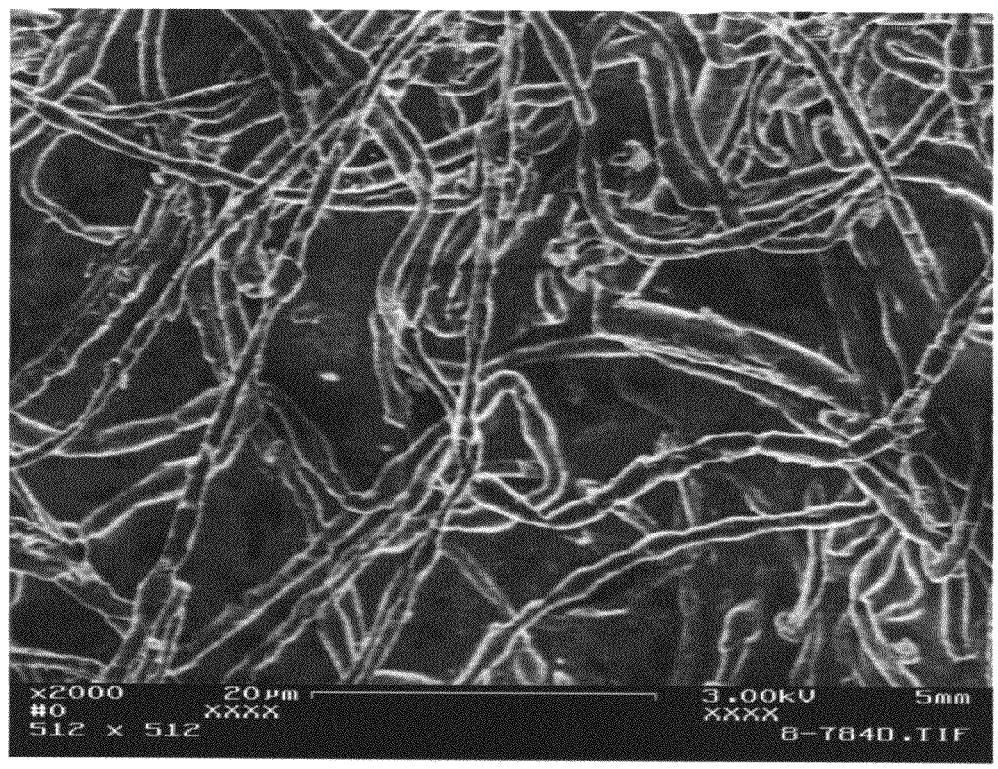

FIG. 4 is an SEM of an electrospun element produced using a low take-up velocity of the collecting wheel and low flow rate of the polymer solution from the syringe. Note the high average pore size and relatively high porosity of the electrospun element. Magnification: ×2,000. Scale bar=20 μm.

Figure 5:
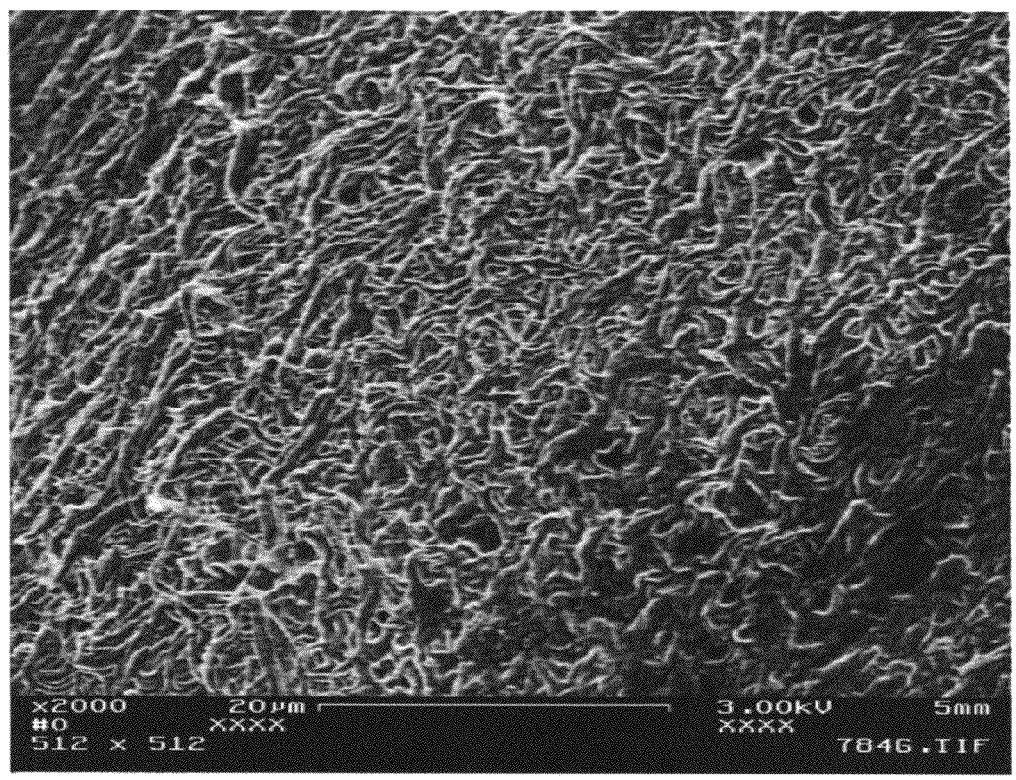

FIG. 5 is an SEM of an electrospun element produced using a high take up velocity of the collecting wheel and high flow rate of the polymer solution from the syringe. Note the low average pore size and low porosity of the electrospun matrix. Magnification: ×2,000. Scale bar=20 μm.

FIGS. 6a-f are SEM images of electrospun elements depicting the effect of polymer concentration on the fiber diameter ($\bar{d}_f$) and permeability (k, darcy units) of the electrospun elements. FIG. 6a—9% PCL, $\bar{d}_f$=0.4μ, k=0.24 darcy; FIG. 6b—10%, PCL, $\bar{d}_f$=0.55μ, k=0.43 darcy; FIG. 6c—11%, PCL, $\bar{d}_f$=0.6μ, k=0.6 darcy; FIG. 6d—13% PCL, $\bar{d}_f$=1μ, k=0.93 darcy; FIG. 6e—14%, PCL, $\bar{d}_f$=1μ, k=1.39 darcy; FIG. 6f—15%, PCL, $\bar{d}_f$=1.5μ, k=1.82 darcy. Note that increasing of the concentration of the polymer results in increased fiber diameter and increased permeability of the electrospun elements. Scale bars in FIGS. 6a-f=2 μm.

DESCRIPTION OF THE PREFERRED EMBODIMENTS

The present invention is of electrospun elements having a continuous or stepwise gradient of porosity, average pore size, weight per volume and/or agents attached, embedded or impregnated therein and of methods of manufacturing and using same. Specifically, the present invention is of PCL, PLA and PGA polymers, mixtures and/or co-polymers which can be used in various combinations to fabricate electrospun scaffolds suitable for guided tissue regeneration, repair and/or implant.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Scaffolds or medical membranes are used in tissue regeneration applications for treating diseased and/or traumatized tissues. Common scaffolds are made of homologous or heterologous tissue-derived materials such as Collagen (e.g., Collagen I or IV), fibronectin elastin and laminin. However, such scaffolds may cause undesirable immunological reactivity, blood coagulation and/or tissue hypertrophy. On the other hand, alloplastic or non-degradable synthetic polymers (e.g., PEG, HA/PCL, PGA, PLGA and PLLA), which display excellent physical properties, lack the bioaffinity and compatibility required for regulation of cell proliferation and tissue organization.

Biocompatible and/or biodegradable hydrogel scaffolds made of various polymers (e.g., collagen based hydrogels) were found suitable for growth and differentiation of bone marrow derived mesenchymal stem cells (MSCs) (Tabata, 2001; Srouji and Livne 2005(a); Tabata et al., 1998; D'Ippolito, 2003; Yoshimoto et al., 2003; Li et al., 2003; 2005; Tuli et al., 2004) and repair of bone defect [Yammamoto et al. 1998; Blumenfeld et al., 2002(a); Blumenfeld et al., 2002(b), Srouji and Livne 2005(a); Srouji et al 2005(b)]. However, although such hydrogel scaffolds are biocompatible and capable of promoting cell differentiation in vitro, their relatively low porosity and low strength prevent their use in clinical applications such as repair of bone fractures in vivo.

Recently, electrospun scaffolds were manufactured from natural or synthetic polymers (e.g., Collagen, PLLA, PGA and PCL). Such scaffolds are made of a single continuous micro to nano-fibrous filament which is collected by a grounded target (e.g., an electrode) as a nonwoven fabric (see for example, U.S. Pat. Appl. No. 20040037813 to Simpson David G, et al; Lee Y H, et al., 2005, Biomaterials. 26: 3165-72; Khil M S, et al., 2005, J. Biomed. Mater. Res. B Appl Biomater. 72: 117-24; Li et al., 2002; Yoshimoto et al., 2003). However, the presently available electrospun scaffolds are not suitable for in vivo guided tissue regeneration and/or repair.

While reducing the present invention to practice and experimentation, the present inventors have uncovered a method of manufacturing an electrospun element having a substantially continuous gradient of porosity, average pore size, weight-per-volume and/or of agents attached to, embedded and/or impregnated therein, which promote proliferation and migration of one population of cells while restricting the migration of another population of cells and thereby capable of guiding tissue regeneration in vivo.

As used herein the phrase "substantially continuous porosity gradient" refers to a change in the porosity of the electrospun element which is preferably below about 10% per 10 μm thickness of the electrospun element.

As is described in Example 2 of the Examples section which follows, the present inventors have uncovered that electrospinning which is performed using a rotating vehicle (e.g., a drum) as a collector electrode can result in an electrospun element with a continuous gradient of porosity.

Thus, according to one aspect of the present invention there is provided a method of manufacturing an electrospun element.

The manufacturing is preferably by an electrospinning process in which one or more liquefied polymers (i.e., a polymer in a liquid form such as a melted or dissolved polymer) are dispensed from a dispenser within an electrostatic field in a direction of a rotating collector. The dispenser can be, for example, a syringe with a metal needle or a bath provided with one or more capillary apertures from which the liquefied polymer(s) can be extruded, e.g., under the action of hydrostatic pressure, mechanical pressure, air pressure and high voltage.

The rotating collector serves for collecting the electrospun element thereupon. Typically, but not obligatorily, the rotating collector has a cylindrical shape (e.g., a drum), however, it will be appreciated that the rotating collector can be also of a planar geometry. The dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Reverse polarity for establishing motions of a negatively charged jet from the dispenser to the collector are also contemplated.

At a critical voltage, the charge repulsion begins to overcome the surface tension of the liquid drop. The charged jets depart from the dispenser and travel within the electrostatic field towards the collector. Moving with high velocity in the inter-electrode space, the jet stretches and solvent therein evaporates, thus forming fibers which are collected on the collector, thus forming the electrospun element.

As used herein, the phrase "electrospun element" refers to an element of any shape including, without limitation, a planar shape and a tubular shape, made of one or more nonwoven polymer fiber(s), produced by a process of electrospinning as further detailed hereinunder. When the electrospun element is made of a single fiber, the fiber is folded thereupon, hence can be viewed as a plurality of connected fibers. It is to be understood that a more detailed reference to a plurality of fibers is not intended to limit the scope of the present invention to such particular case. Thus, unless otherwise defined, any reference herein to a "plurality of fibers" applies also to a single fiber and vice versa.

The polymer fibers of the electrospun element can be arranged on a single layer, but, more preferably, the fibers define a plurality of layers hence form a three dimensional structure. The polymer fibers can have a general random orientation, or a preferred orientation, as desired e.g., when the fibers are collected on a cylindrical collector such as a drum, the polymer fibers can be aligned predominantly axially or predominantly circumferentially. Different layers of the electrospun element can have different orientation characteristics. For example, without limiting the scope of the present invention to any specific ordering or number of layers, the fibers of a first layer can have a first predominant orientation, the fibers of a second layer can have a second predominant orientation, and the fibers of third layer can have general random orientation.

In various exemplary embodiments of the invention, at least one parameter is varied during the electrospinning process in a substantially continuous manner.

The phrase "at least one parameter" refers to any physical parameter involved in the electrospinning process. Examples without limitations for such parameter include at least one of: the velocity of the rotating collector, the characteristic of the electrostatic field vector (magnitude and/or direction), the size of the capillary apertures of the dispenser (e.g., the size of a needle attached to the dispenser), the numbers of dispensers, the dispensing flow rate of the at least one liquefied polymer the viscosity, concentration and/or conductivity of the liquefied polymer, the concentration of the agents attached to the liquefied polymer in each of the dispensers and the concentration of charge control agent (e.g., a miscible salts).

The characteristic of the electrostatic field vector can be varied during the electrospinning process in more than one way. In one preferred embodiment, the variation of the electric field is effected by varying, preferably continuously, the distance between the dispenser and the collector; in another preferred embodiment, the variation of the electric field is effected by varying, preferably continuously, the potential difference between the dispenser and the collector; in an additional embodiment, the variation of the electrostatic field is effected by varying both the distance and the potential difference in a substantially continues manner.

As used herein, the phrase "substantially continuously varying" refers to gradually changing or modifying. Preferably, such a gradual change is characterized by imperceptible (i.e., extremely slight, gradual, or subtle) increments. One example of "substantially continuously varying" is monotonically varying the at least one parameter described hereinbelow. It will be appreciated that the variation can be at a constant rate, in which case the effect of such variation is linear or at a variable rate in which case the effect is nonlinear.

The advantage of using a rotating collector (such as a drum) for collecting the polymer fibers is that, as uncovered by the present inventors, such configuration allows a control over the porosity of the electrospun element.

As used herein the term "porosity" refers to the ratio of the volume of interstices (i.e., pores) of a material to the volume of its mass. Such a ratio can be fixed and unchanged along the depth and/or surface of the electrospun element or can vary along the depth and/or surface of the electrospun element.

As will be appreciated by one ordinarily skilled in the art, the porosity and the pore size of the electrospun element are two related physical quantities. Nevertheless, these physical quantities are not identical, because the porosity depends on both the number of pores and the average pore size. Thus, different electrospun elements (or different portion of the same electrospun element) can have the same pore size yet different porosity and vice versa. For example, a first portion of the electrospun element having N pores of size S per unit area has a smaller porosity than a second portion having $N+\Delta$ ($\Delta>0$) pores of the same size S per unit area.

Independent variation of the average pore size and the porosity of the electrospun element can be achieved, for example, by varying both the density and the diameter of the fibers, substantially simultaneously. Variation of fiber diameter can be achieved, for example, by varying the electrostatic field, the polymer solution concentration, environmental temperature, the diameter of the dispenser's apertures (e.g., using a shutter), the flow rate of the polymer (e.g., by a syringe pump, or by controlling the back pressure), the viscosity of the polymer (e.g., by continuously adding viscous agent to the polymer solution). Also, as will be appreciated by one of ordinary skill in the art, the fiber diameter depends on the concentration of the polymer solution which affects the extent of liquid evaporation from the jets prior to their sedimentation on the collector.

A substantially continuous variation of the velocity of the rotating collector, results in a substantially continuous variation of the density and/or spatial distribution of the fibers on the collector. Thus, as the collector continues to rotate, the fibers are piled thereon at a substantially continuously varying density resulting in a porosity gradient along the radial and/or circumferential direction of the collector. Additionally, a motion of the dispenser along the longitudinal direction of the collector can be established so as to form a porosity gradient also along the longitudinal direction. A porosity gradient which is achieved by angular velocity variation is typically accompanied by a pore-size gradient. For example, as is shown in FIGS. 4 and 5 and is described in Example 2 of the Examples section which follows, high velocity of the rotating collector [e.g., a speed of 60 meter/minute] linear velocity resulted in low porosity and low average pore size (FIG. 5). On the other hand, low velocity (e.g., a speed of 1 meter/minute linear velocity) resulted in high porosity and high average pore size (FIG. 4).

For example, an electrospun element with a gradient porosity can be manufactured as follows. A 5 ml syringe or more containing 10% PCL in DCM/DMF (1:1) is positioned at a distance of 25 centimeters from the wheel rim including the collecting electrode. The polymer solution in the syringe is charged with 18 kV and the polymer solution flows from the syringe at an initial flow rate of 0.5 ml per hour. The initial speed of the wheel is 0 meter/minute linear velocity and is changed gradually at intervals of 6 meter/minute linear velocity every 10 minutes to a final speed of 96 meter/minute linear velocity. Such conditions result in an initial porosity of about 95% and a final porosity of about 75%

Additionally or alternatively, changing the electrostatic field (e.g., by varying the distance and/or voltage difference between the dispenser and collector) modifies the fiber diameter and the polymer flow rate. For example, changing the voltage per cm from 0.2 kV/cm to 1 kV/cm an/or the flow rate from 0.1 ml per hour to 2 ml per hour.

Additionally or alternatively, changing the size or shape of the dispenser (e.g., the aperture diameter of the needle) affects the fiber diameter. For example, using a voltage of 18 kV and a needle diameter of 270 μm can yield a constant flow rate of 0.1 ml/hour and a fiber diameter of 400 nm.

In various exemplary embodiments of the invention the fiber diameter can be increased from an initial diameter of 400 nm to a final diameter of about 2000 nm.

Additionally or alternatively, changing the distance between the dispenser and the rotating collector (e.g., the distance between the syringe needle and the wheel rim) affects the porosity of the electrospun element. For example, a polymer solution which is charged with 18 kV and flows at a rate of 0.1 ml/hour at a distance of 20 cm results in an electrospun element with 85% porosity. On the other hand, using the same conditions (i.e., 18 kV and flow rate of 0.1 ml/hour) at a distance of 45 cm, results in an electrospun element having about 93% porosity. It will be appreciated that a gradual increase of the distance between the dispenser and the collector electrode will result in a gradual porosity. Thus, increments of about 2 cm in the distance are expected to result in a change of about 1% in the porosity of the electrospun element of the present invention.

Thus, by substantially continuously varying a parameter as described hereinabove, the electrospun element of the present invention is characterized by a substantially continuous porosity gradient.

In various exemplary embodiments of the invention the porosity is a monotonic function. For example, the porosity can continuously increase inward along a line connecting one external surface of the electrospun element with the other.

According to one preferred embodiment of the present invention the continuous porosity gradient has a maximal porosity of about 95% and a minimal porosity of about 50%.

According to yet another preferred embodiment of the present invention the continuous porosity gradient has a maximal porosity of about 90% and a minimal porosity of about 50%, more preferably, a maximal porosity of about 85% and a minimal porosity of about 55%, more preferably, a maximal porosity of about 80% and a minimal porosity of about 60%, more preferably, a maximal porosity of about 80% and a minimal porosity of about 65%, more preferably, a maximal porosity of about 75% and a minimal porosity of about 70%.

It will be appreciated the parameters described hereinabove can be discretely varied to result in a stepwise gradient of porosity. A stepwise porosity gradient suitable for the present embodiment includes discrete porosity variations at about 5% intervals.

It will be appreciated that the teachings of the method according to this aspect of the present invention can be used to manufacture an electrospun element having a gradient of average pore size along at least a portion thereof. Such a gradient of average pore size can be continuous or step wise gradient of average pore size.

As used herein the phrase "pore size" refers to the area of a pore at a given plane which is formed between the fibers of the electrospun element. The pore size distribution and dimensions of the electrospun element of the present invention can be determined using a mercury porosimeter, a confocal microscope or by other known methods. For example, a mercury porosimeter can be used to determine the permeability of the electrospun element in Darcy units according to the Darcy equation: $K=\Delta L/\Delta P$; wherein "L" is thickness of the electrospun element; and "P" is the pressure of the mercury which passes through the electrospun element. Thus, a higher K value represents better permeability across the electrospun element.

Another way of quantitating the pore size is by calculating the diameter of the pore at a single plane, using e.g., a confocal microscope. Preferably, since the pores formed in the electrospun element are not of a perfect circle-shape, the diameter of the pore measured according to this aspect of the present invention is the largest diameter at the measured plane.

According to preferred embodiments of the present invention, the gradient of average pore size has a maximal average pore diameter of about 200 μm and a minimal average pore diameter of about 0.1 μm. Preferably, such a gradient of average pore size has a maximal average pore diameter of about 200 μm and a minimal average pore diameter of about 1 μm, more preferably, such a gradient of average pore size has a maximal average pore diameter of about 200 μm and a minimal average pore diameter of about 10 μm.

As is mentioned before, electrospinning results in at least one continuous fiber which is randomly oriented and thus forms the electrospun element. Several parameters may affect the diameter of such a fiber. These include, the size of the dispensing hole of the dispenser, the dispensing rate, the strength of the electrostatic field, the distance between the dispenser and/or the concentration of the polymer used for fabricating the electrospun element.

According to one embodiment of the present invention, the electrospun element of the present invention exhibits a uniform fiber diameter having a variance of about 10% or less.

On the other hand, it will be appreciated that gradual change of at least one of the abovementioned parameters may result in an electrospun element having a gradient of average fiber diameter along at least a portion of the electrospun element. For example, as is shown in FIGS. 6a-f and is described in Example 2 of the Examples section which follows, changing the concentration of the liquefied polymer used for fabricating the electrospun element can result in different fiber diameters.

Thus, according to another embodiment of the present invention, the gradient of average diameter is a continuous gradient of average diameter.

It will be appreciated that in order to form a gradient of an average diameter, the polymer can be provided by multiple dispensers, each containing a different concentration of the polymer and/or copolymer.

It will be appreciated that the fiber comprising the electrospun element can be of a core-shell structure (e.g., a core which is formed from one polymer and a shell, which surrounds the core and is formed from another polymer). Fibers of a core-shell structure can be manufactured using methods known in the art such as using a unified double syringe structure (e.g., see Z. Sun, E. Zussman, A. L. Yarin, J. H. Wendorff, A. Greiner, "Compound Core/shell Polymer Nanofibers by Co-Electrospinning", *Advanced Materials,* 15, 22:1929-1936, 2003). It will be appreciated that the fiber comprising the electrospun element can be also a hollow fiber. As is used herein, the phrase "hollow fiber" refers to a fiber with a core-shell structure from which the core is removed. Such fibers can have an inner diameter of less than about 1 µm. Removal of the core from the core-shell structure can be effected using methods known in the art such as by incubating the fibers of the electrospun element in a solvent (e.g., water) capable of dissolving the polymer (or co-polymer) used to fabricate the core but incapable of dissolving the polymer (or co-polymer) used to fabricate the shell. Additionally or alternatively, removal of the core polymer from the shell can be effected by heating the fibers of the electrospun element at a temperature selected capable of melting or evaporating the polymer (or copolymer) used to fabricate the core but not the polymer (or co-polymer) used to fabricate the shell.

It will be appreciated that changes of the fiber diameter may affect the average fiber weight-per-volume of the electrospun element. Thus, a gradual change of the fiber diameter (by e.g., gradually varying the strength of the electrostatic field) can result in a gradient of fiber weight-per-volume.

It will be appreciated that a gradient of fiber weight-per-volume can be achieved by changing the flow rate and/or concentration of the polymer solution from the syringe. For example, a polymer solution, which is charged at 1.0 kV/cm, is dispensed at an initial flow rate of 0.1 ml/minute and gradually increases at increments of 0.1 ml/minute until a flow rate of 1.0 ml/minute is achieved.

In addition, a gradient of fiber weight-per-volume can be also achieved by using more than one syringe alternatively or together with variable polymer concentrations in each syringe. For example, electrospinning is performed using two syringes; one syringe contains a solution of 12% PCL/PLA and a second syringe contains a solution of 6% PCL/PLA. Electrospinning begins by dispensing the solution of the first syringe, which is charged at 1.2 kV per cm, for 120 minutes at a flow rate of 0.1 ml/minute, following which, dispensing is effected from both syringes (which are charged with the same voltage per cm) for 120 minutes. However, while the flow rate of the solution from the first syringe continues at 0.1 ml/minute, the flow rate of the solution from the second syringe gradually increases from 0.1 ml/minute to 1 ml/minute in increments of 0.01 ml/minute. Following 240 minutes, dispensing is completed.

Thus, the gradient of average fiber weight-per-volume can be a continuous or step wise, depending on the rate and increments of changing the flow rate and/or the concentration of the polymer solutions used.

The phrase "at least one liquefied polymer" refers to any polymer, polymers or co-polymers which are in a liquid form (e.g., a soluble polymer in solution or a melted polymer). The polymer used by the present invention can be a natural, synthetic, biocompatible and/or biodegradable polymer.

The phrase "synthetic polymer" refers to polymers that are not found in nature, even if the polymers are made from naturally occurring biomaterials. Examples include, but are not limited to, aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use in the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid and alginate.

As used herein, the phrase "co-polymer" refers to a polymer of at least two chemically distinct monomers. Non-limiting examples of co-polymers include, PLA-PEG, PEGT/PBT, PLA-PGA PEG-PCL and PCL-PLA.

The phrase "biocompatible polymer" refers to any polymer (synthetic or natural) which when in contact with cells, tissues or body fluid of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by proteases. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Examples of biodegradable polymers include, but are not limited to, collagen (e.g., Collagen I or IV), fibrin, hyaluronic acid, polylactic acid (PLA), polyglycolic acid (PGA), polycaprolactone (PCL), polydioxanone (PDO), trimethylene carbonate (TMC), polyethyleneglycol (PEG), Collagen, PEG-DMA, Alginate, chitosan copolymers or mixtures thereof.

According to one embodiment, the liquefied polymer can be made of one polymer or more, each can be a polymer or a co-polymer such as described hereinabove.

According to one embodiment of the present invention, the liquefied polymer of the present invention is a mixture of at least one biocompatible polymer and a co-polymer (either biodegradable or non-biodegradable).

It will be appreciated that the electrospun element of the present invention can be used as a scaffold or membrane such as for guiding tissue regeneration.

As used herein the phrase "scaffold" refers to a two-dimensional or a three-dimensional supporting framework. The scaffold of the present invention is composed of electrospun fibers, each fiber composed of at least one polymer as described hereinabove. It will be appreciated that the scaffold of the present invention can be embedded within, or formed around, another scaffold or hydrogel and various configurations of electrospun elements and hydrogels can be composed.

As used herein, the term "hydrogel" refers to any material with molecular net structure in which water constitutes more than 50%. For example, a hydrogel can include a cross-linked polymer with a water constitute of at least 70%. Non-limiting examples of hydrogels which can be used along with the present invention include, a Collagen hydrogel, a PEG hydrogel, a PEG-DMA hydrogel, and an Alginate hydrogel.

For example, a composite scaffold of an electrospun element and a hydrogel can be prepared by electrospinning a first polymer solution capable of forming a hydrogel (e.g., Collagen), followed by electrospinning of a second polymer (e.g., a co-polymer of PCL-PLA) on the top of the first electrospun element. Following electrospinning, the composite electrospun element is soaked in water, resulting in absorption of water by the first electrospun layer (e.g., the Collagen) and the formation of a hydrogel layer (made of the first polymer) underneath the electrospun fibers (made of the second polymer).

Alternatively, a first polymer solution (e.g., Collagen) can be soaked in water to form a hydrogel and electrospinning is performed on the top of the hydrogel with a second polymer solution (e.g., PCL-PLA).

Similarly, an electrospun scaffold can be layered within or on a hydrogel layer. For example, PCL-PLA electrospun scaffold was layered with collagen hydrogels membrane (Example 1 of the Examples section which follows).

Similarly, electrospinning can be effected using a polymer solution capable of forming a hydrogel (e.g., Collagen) which is mixed with another polymer solution (e.g., a co-polymer of PCL-PLA) which is incapable of forming a hydrogel. Following electrospinning the electrospun element can be soaked in water and a hydrogel can be formed. Still additionally or alternatively, electrospinning can be formed using the core-shell configuration in which the core polymer is selected from a polymer capable of forming a hydrogel (e.g., Collagen) and the shell polymer is selected incapable of forming a hydrogel, or vice versa.

It will be appreciated that the electrospun element of the present can also form a complex structure of two surfaces defining a volume therebetween.

Thus, according to preferred embodiments of the present invention, the article of manufacturing includes an electrospun element having a first surface and a second surface defining a volume therebetween, wherein an average pore size close to the first surface as well as the chemical and biological characteristics are selected so as to allow migration of at least one population of cells therethrough into the volume, and an average pore size close to the second surface as well as the chemical and biological characteristics are selected so as to restrict migration of at least one population of cells therethrough into the volume.

The term "volume" as used herein refers to an interface formed between to two surfaces. Such a volume can be used, for example, for proliferation and/or differentiation of cells which are seeded, as described hereinbelow, within the electrospun element.

It will be appreciated that the surfaces of the electrospun element can be made from either the same or different polymers and/or materials. Additionally and/or alternatively, the surfaces can have the same or different structure, porosity, average pore size, fiber weight-per-volume and/or agents (e.g., chemical, biological and/or mineral) attached thereto, embedded or impregnated therein.

Thus, the scaffold of the present invention can be used to support cell growth, attachment, spreading, and thus facilitate cell growth, tissue regeneration and/or tissue repair. Such a scaffold is therefore being seeded with cells capable of proliferating and/or migrating therethrough.

Preferably, the electrospun element or the scaffold composed of the electrospun element with an hydrogel is placed in a culture medium for promoting proliferation of at least one population of cells being in contact with the electrospun element. Such one population of cells can be for example, osteoblast cells, endothelial cell or stem cells.

The culture medium used by the present invention can be any liquid medium which allows at least cell survival. Such a culture medium can include, for example, salts, sugars, amino acids and minerals in the appropriate concentrations and with various additives and those of skills in the art are capable of determining a suitable culture medium to specific cell types. Non-limiting examples of such culture medium include, phosphate buffered saline, DMEM, MEM, RPMI 1640, McCoy's 5A medium, medium 199 and IMDM (available e.g., from Biological Industries, Beth Ha'emek, Israel; Gibco-Invitrogen Corporation products, Grand Island, N.Y., USA).

It will be appreciated that to enable proliferation, migration and/or differentiation of the cells being seeded in the electrospun element of the present invention, the culture medium is preferably supplemented with various antibiotics (e.g., penicillin and Streptomycin), growth factors or hormones, specific amino acids (e.g., L-glutamin) cytokines and the like.

For example, as is shown in Example 1 of the Examples section which follows, the culture medium can include dexamethasone which is capable of inducing the proliferation and differentiation of bone marrow derived mesenchymal stem cells (MSCs) into osteoblasts.

According to one embodiment of the present invention, the culture medium includes a mineralizing agent. The phrase "mineralizing agent" refers to an agent including at least one mineral capable of forming mineral-containing substance, e.g., mineral containing tissue such as a bone. Non-limiting examples of such agents include, calcium which can form calcium phosphate and hydroxyapatite. Preferably, the mineralizing agent is capable of supporting the formation and/or remodeling of a bone tissue including, but not limited to a dental tissue, a bone, a vertebrae and the like.

It will be appreciated that the continuous porosity gradient of the electrospun element of the present invention allows the migration of at least one population of cells (e.g., osteoblast cells, endothelial cells) through one side of the electrospun element and, on the other hand, restricts the migration of at least another population of cells (e.g., fibroblast cells) through a second side of the electrospun element.

Similarly, an electrospun element having a continuous gradient of average pore size can be selected such that it allows the migration of at least one population of cells (e.g., osteoblast cells, endothelial cells) through one side of the electrospun element and, on the other hand, restricts the migration of at least one population of cells (e.g., fibroblast cells) through a second side of the electrospun element.

Similarly, an electrospun element having a continuous gradient of fiber weight-per-volume can be selected such that it allows the migration of at least one population of cells (e.g., osteoblast cells, endothelial cells) through one side of the electrospun element and, on the other hand, restricts the migration of at least one population of cells (e.g., fibroblast cells) through a second side of the electrospun element.

In order to increase the bioaffinity and recognition of the cells proliferating and/or migrating through the electrospun element (e.g., a scaffold containing an electrospun element), and/or to increase the therapeutic potential of the scaffold, such an electrospun element further includes at least one agent. Such an agent can be a biological agent such as an amino acid, a peptide, a polypeptide, a protein, a DNA, an RNA, a lipid and/or a proteoglycan.

Suitable proteins which can be used along with the present invention include, but are not limited to, extracellular matrix proteins [e.g., fibrinogen, Collagen, fibronectin, vimentin, microtubule-associated protein 1D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-α, fibroblast growth factor-acidic, bone morphogenic protein, fibroblast growth factor-basic, erythropoietin, thrombopoietin, hepatocyte growth factor, insulin-like growth factor-1, insulin-like growth factor-II, Interferon-β, platelet-derived growth factor, Vascular Endothelial Growth Factor and angiopeptin], cytokines [e.g., M-CSF, IL-1beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

Additionally and/or alternatively, the at least one agent used by the present invention is an antiproliferative agent (e.g., rapamycin, paclitaxel, tranilast, Atorvastatin and trapidil), an immunosuppressant drug (e.g., sirolimus, tacrolimus and Cyclosporine) and/or a non-thrombogenic or anti-adhesive substance (e.g., tissue plasminogen activator, reteplase, TNK-tPA, glycoprotein IIb/IIIa inhibitors, clopidogrel, aspirin, heparin and low molecular weight heparins such as enoxiparin and dalteparin).

Preferably, the at least one agent used by the present invention is a chemical or mineral which is added to the electrospun element in order to improve its biological properties. For example, the electrospun element can be embedded with, attached to or impregnated with minerals which promote bone formation and/or mineralization such as calcium sulfate and/or Hydroxyapatite.

The at least one agent of this aspect of the present invention can be attached to at least a portion of the electrospun element. Such attachment can be performed using e.g., cross-linking (chemical or light mediated) of the at least one agent with the polymer solution or the electrospun fiber formed therefrom (e.g., PEG-DMA, PLA and the agent). Additionally or alternatively, the at least one agent can be embedded in electrospun micro or nanofibers having the core-shell structure essentially as described in Sun, 2003 (Supra). Still additionally or alternatively the at least one agent can be impregnated in the electrospun element by soaking the electrospun element or at least a portion of the polymer fibers forming the electrospun element in a solution containing such an agent.

It will be appreciated that the at least one agent which is attached to, embedded, mixed or impregnated in the electrospun element can form a gradient along at least a portion of the electrospun element. Such a gradient can be a continuous or step-wise gradient and can be formed, for example, by changing the concentration of the agent in the liquefied polymer. For example, the syringe can have two or more feeding sources of liquefied polymers with variable concentrations of the agent attached to or mixed with. To form a gradient, each feeding source is used for a predetermined time (e.g., a few seconds or minutes). For example, the different feeding sources can include various concentrations of the agents attached to or mixed with the polymer (e.g., 1%, 2%, 3% and the like, although smaller increments can be used as well) and following predetermined time periods (e.g., 1 minute) a different feeding source is utilized. To form a step-wise gradient, several feeding sources are used, each containing the polymer solution with a different concentration of agent (e.g., 1%, 10% and 20%) and for a time period sufficient for forming a "layer" of the agent. Additionally or alternatively, the gradient of the at least one agent can be formed by impregnating at least a portion of the polymer fibers with increasing concentrations of the agent. Still additionally or alternatively, the gradient of the at least one agent can be formed by embedding increasing concentrations of the agent in the electrospun element.

For example, retinoic acid (RA), which is capable of promoting proliferation, can be used at a high concentration at the lower layer and at a low concentration at the upper layer of the electrospun element to thereby provide an electrospun element with differential biological properties. Thus, the lower layer of the electrospun element is capable of promoting proliferation and angiogenesis, while the higher layer of the electrospun element, which is devoid of RA or, alternatively, includes another agent such as a differentiation factor, is capable of inhibiting proliferation.

Thus, the electrospun element of the present invention can have a gradient of porosity, average pore size, or fiber weight-per-volume with or without a gradient of at least one agent attached to, embedded or impregnated therein.

Additionally or alternatively, the electrospun element of the present invention can be of a uniform porosity, average pore size or fiber weight-per-volume yet with a gradient of at least one agent attached to, embedded or impregnated therein.

While further reducing the present invention to practice and experimentation, the present inventors have uncovered that a PCL-PLA and/or PLA-PLGA electrospun scaffolds are highly suitable for guiding bone formation and that such a scaffold can be used in bone regeneration and/or repair.

As is shown in FIGS. 1*c-f* and is described in Example 1 of the Examples section which follows, bone marrow derived MSCs which were seeded in the presence of an osteogenic medium (DMEM medium supplemented with 15% fetal calf serum (FCS), 20 mM L-glutamin, Pen-Strep (100 U/ml penicillin, 100 µg/ml streptomycin), 100 µg/ml ascorbic acid, 10 mM sodium β-glycerophosphate and $10^{-8}$ M dexamethasone) in the PCL-PLA electrospun scaffold (in a 3:1 ratio, respectively), were capable of proliferating and differentiating into osteoprogenitor cells capable of matrix deposition. In addition, as is further shown in FIGS. 2*c-d* and 3*a-d* and is described in Example 1 of the Examples section which follows, such cells adhered to the matrix (e.g., scaffold) and deposited a dense extracellular matrix (ECM) which was found to contain calcium and phosphate ions at a ratio of 1.8, similar to that observed in an intact bone.

Thus, according to yet an additional aspect of the present invention there is provided a scaffold. The scaffold comprising an electrospun element consisting of PCL, PLA, and/or PGA polymers and/or their co-polymers, whereby when seeded with bone marrow derived stem cells in an osteoblast differentiation inducing medium containing at least one mineral the matrix is populated with osteoblasts and mineralizes so as to transform into a mineralized scaffold.

As used herein the phrase "at least one mineral" refers to a mineral needed for bone formation and/or regeneration. Non-limiting examples of such a mineral include sodium β-glycerophosphate, ascorbic acid, and calcium phosphate.

Similarly, the phrase "mineralized scaffold" refers to a scaffold containing at least one form of the at least one mineral included in the medium. For example, a calcium phosphate mineral can be formed in the presence of sodium β-glycerophosphate and calcium chloride (which is included in the DMEM medium).

Figure 1:
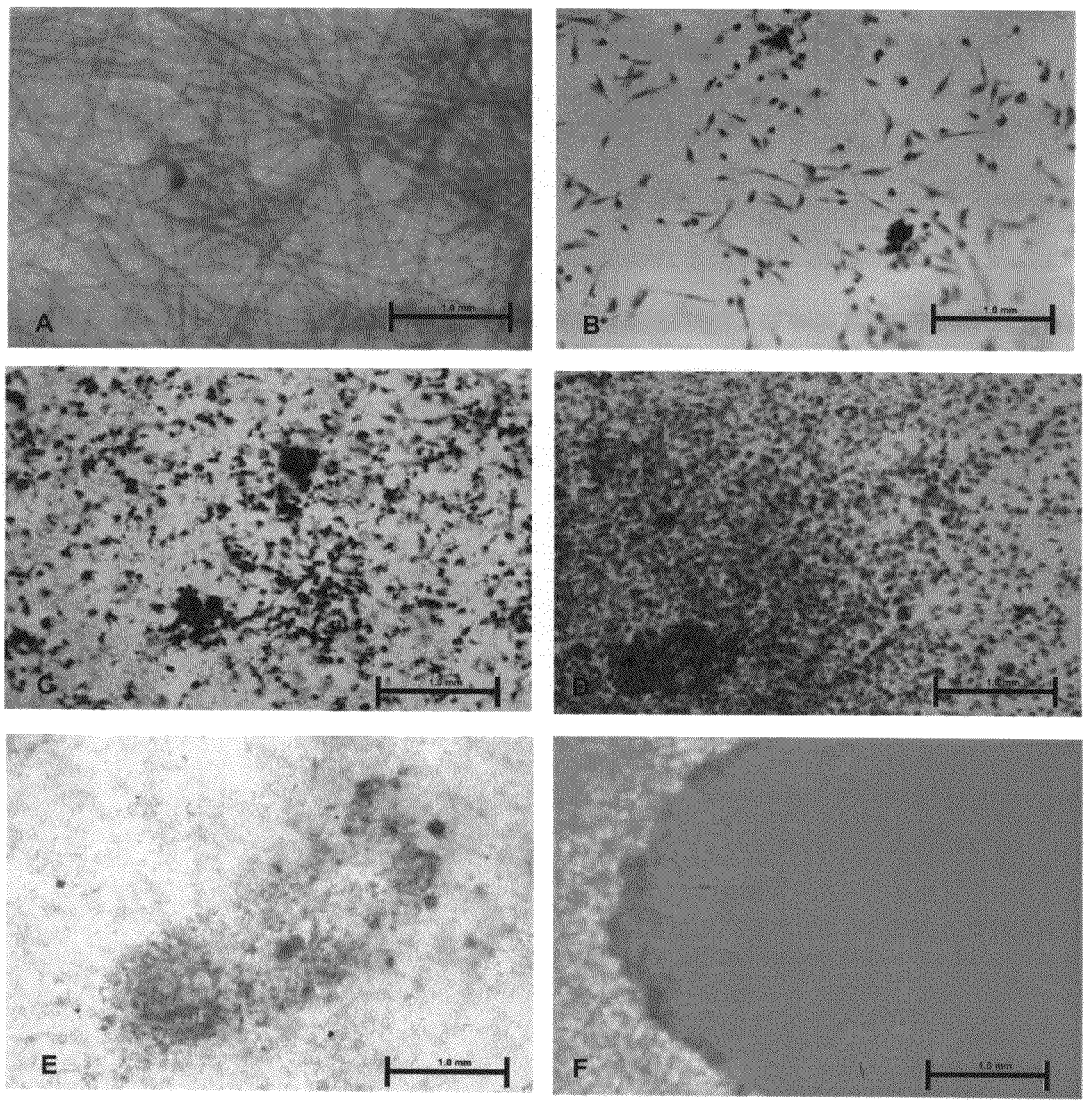
Figure 2:
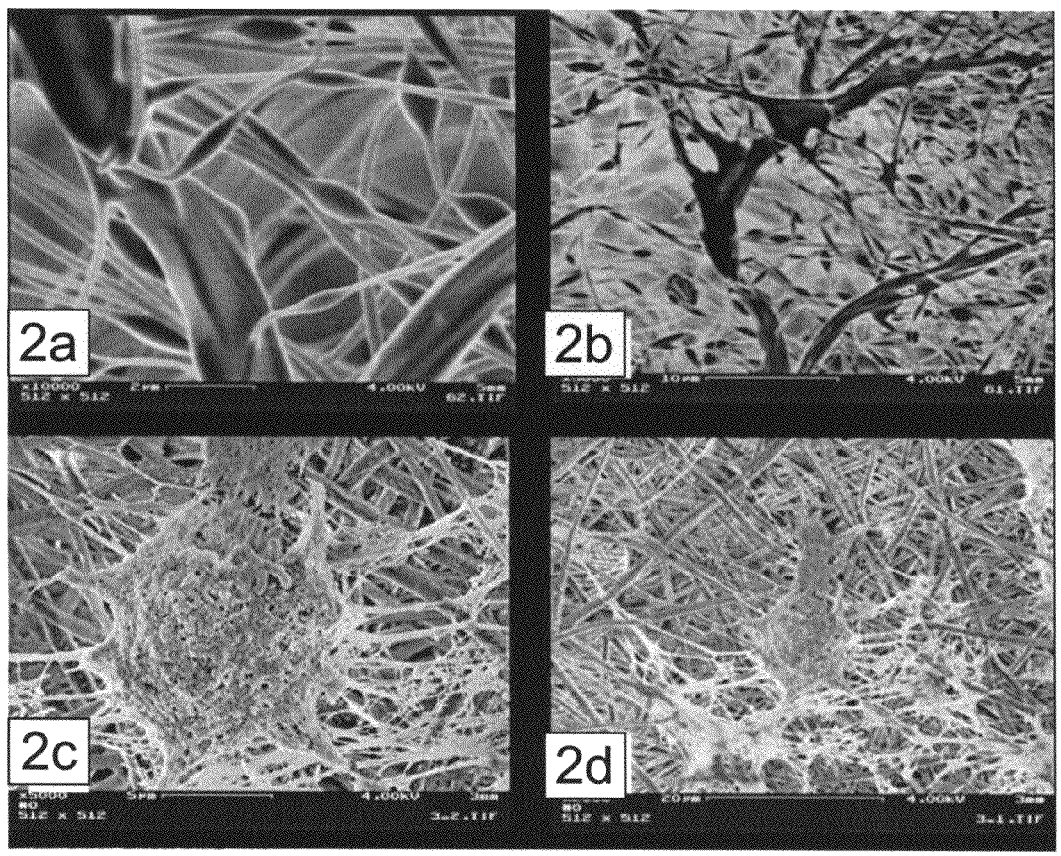
Figure 3:
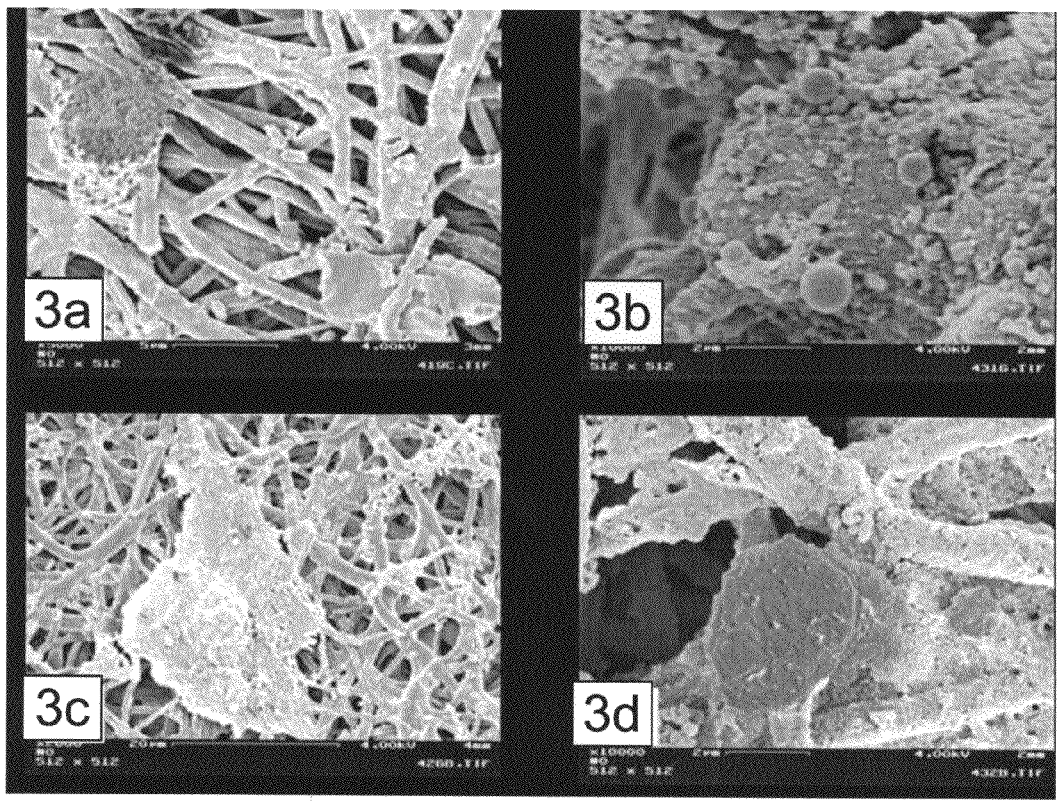

As is shown in FIGS. 1-3 and is described in Example 1 of the Examples section which follows, even following 3 weeks in culture in the presence of MSCs and the osteogenic medium, the PCL-PLA scaffold of the present invention was devoid of fibroblast cell. It will be appreciated that restricting the migration of fibroblast cells into a scaffold promotes proper bone regeneration and/or repair.

It will be appreciated that the PCL, PLA, and/or PGA polymers can be provided at various weight ratios.

According to one embodiment of the present invention, the PCL, PLA, and/or PGA polymers are provided at weight ratios such that the weight of the PLA is higher than the weight of the PCL and/or PGA. Suitable weight ratios for the PCL:PLA can be for example, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, at least 1:9, respectively. Suitable weight ratios for the PCL:PGA can be for example, about 1:1.5, respectively.

According to yet another embodiment of the present invention, the PCL and PLA polymers are provided at a weight ratio such that the weight of the PLA is lower than the weight of the PCL. Suitable weight ratios for the PCL:PLA can be for example, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, at least 9:1, respectively. Suitable weight ratios for the PLA:PLGA can be for example, about 1:1 or 1:2 ratios, respectively. Suitable weight ratios for the PCL:PLGA can be for example at 1:1 or 1:2 ratios, respectively.

According to preferred embodiments of the present invention, the electrospun element of the scaffold of the present invention is characterized by a predetermined average pore size selected so as to restrict migration of fibroblast cells therethrough.

Such a predetermined pore size can be for example, a pore having a diameter lower than 1 μm, more preferably, lower than 0.2 μm, even more preferably, a pore having a diameter of about 0.1 μm.

On the other hand, the predetermined average pore size is selected so as to allow penetration of oxygen molecules therethrough. Such a predetermined average pore size can be of a diameter of at least 0.1 μm, more preferably, at least 0.5 μm, even more preferably, about 1 μm.

Similarly, the predetermined average pore size is selected so as to allow penetration of nutrients therethrough. Such a predetermined average pore size can be of a diameter of at least 0.1 μm, more preferably, at least 1 μm, even more preferably, about 10 μm.

According to one embodiment of the present invention, the electrospun element is characterized by a predetermined average pore size having a diameter selected from about 0.1 micrometer to about 200 micrometer, more preferably, from 0.5 micrometer to about 200 micrometer, more preferably, from 1 μm to about 200 μm, more preferably, from 10 nanometer to about 200 μm, even more preferably, from 30 μm to about 200 μm.

It will be appreciated that the electrospun element according to this aspect of the present invention can have a relatively uniform pore size with a variance of pore diameter of about 20% or less than the average pore diameter.

The porosity of the electrospun element of the present invention can be of at least 50%, more preferably, at least 55%, more preferably, at least 60%, more preferably, at least 65%, more preferably, at least 70%, more preferably, at least 75%, more preferably, at least 80%, more preferably, at least 85%, more preferably, at least 90%, even more preferably, about 95% porosity.

According to preferred embodiment of the present invention, the electrospun element of the present invention forms a porous membrane.

As used herein the term "membrane" refers to a pliable sheet (usually thin) of material serving as a semi-permeable covering, i.e., enables the passage of one type of material or cells and not the other type of material or cell. For example, the membrane of the present invention [i.e., the PCL:PLA (at a 3:1 ratio) electrospun element] enables the migration of osteoblast cells but restrict the migration of fibroblast cells.

According to another embodiment of the present invention, the electrospun element of the present invention exhibits a tubular structure.

While further reducing the present invention to practice, the present inventors have uncovered that passing an electrical spark through an electrospun element results in holes through at least part of the electrospun element.

Thus, according to yet an additional aspect of the present invention there is provided a method of perforating an electrospun element. The perforation can be done, for example, by an electrical spark, which can be generated by any electrical spark producing element, such as, but not limited to, a needle-like electrode. The electrical spark can vary depending on the applied voltage, its duration and the distance between the electrode and the electrospun element.

The electrical spark is produced with an electric field which is sufficient to generate air breakdown. At normal conditions, such breakdown occurs at about 30 kV/cm. Thus, according to a preferred embodiment of the present invention the electrical spark is produced by generating an electric field of about 30 kV/cm.

The electric field is preferably generated by a potential difference of at least 10 kV, more preferably, at least 15 kV.

According to preferred embodiments of the present invention the breakdown field is generated by positioning the electrode at a distance of about 10 mm, more preferably, at a distance of 5 mm, even more preferably, at a distance of 1 mm from the electrospun element.

According to preferred embodiments of the present invention, the voltage used to provide the electrical spark is provided for a time period of about 5 seconds, more preferably, for a time period of about 1 second, even more preferably, for a time period of 0.1 second For example, an electrospun element made of PCL/PLA at a 3:1 ratio, respectively, with a total thickness of 200 μm can be perforated by positioning the electrospun element between a high voltage electrode (e.g., at 18 kV) and a ground electrode at a distance of about 1 mm.

While further reducing the present invention to practice, the present inventors have uncovered that passing a heated puncturing element through en electrospun element results in a perforated electrospun element.

Thus, according to yet an additional aspect of the present invention, there is provided a method of perforating an electrospun element. The method is effected by passing a puncturing element through at least a portion of the electrospun element to thereby obtain a perforated electrospun element.

As used herein, the phrase "puncturing element" refers to any sharp and pointed element, preferably a metal implement which is capable of being heated and thus puncturing (i.e., making a hole) the electrospun element. Non-limiting examples of such puncturing elements include, a metal needle and a metal pin.

According to preferred embodiments of the present invention, the puncturing element is heated to a temperature of at least 90° C., more preferably, at least 91° C., more preferably, at least 92° C., more preferably, at least 93° C., more preferably, at least 94° C., more preferably, at least 95° C., more preferably, at least 96° C., more preferably, at least 97° C., more preferably, at least 98° C., more preferably, at least 99° C., even more preferably, at least 100° C., say about 100° C., about 101° C., about 102° C.

Passing the puncturing element according to the method of this aspect of the present invention can be effected for a time period of 0.1-10 seconds, more preferably, for a time period of 1-5 seconds.

For example, the electrospun scaffold can be perforated using a heated needle pillow (to about 100° C. in the case of the PCL/PLA electrospun scaffold described in Example 1 of the Examples sections which follows). It will be appreciated that the scaffold can be perforated by piercing, i.e., producing a single hole or an array of holes.

It will be appreciated that perforating an electrospun elements can be also effected by a pulsed or continues laser beam. The laser beam can be generated by any laser device capable of providing laser radiation which ablate or melt the polymer fibers to some extent. These include, but are not limited to, the following laser devices: Excimer laser device, Kr based laser device, Xe based laser device, Er based laser device, Ho:YAG laser device, carbon-dioxide laser device, Nd based laser device and laser diode device. Kr based laser devices include, but are not limited to krypton-fluoride (KrF) laser devices. Xe based laser devices include, but are not limited to xenon-fluoride (XeF) laser devices. Er based laser devices include, but are not limited to, Er:YAG, Er:YSGG, Er:glass and the like. Nd based laser devices include, but are not limited to, Nd:YAG, Nd:YLF, Nd:glass and the like. Also contemplated are $CO_2$ and Dye laser devices.

For example, perforation of an electrospun element is performed using a pulsed laser beam at a specific energy (e.g., 200 Watt) which is provided at a specific rate (e.g., 200 Hz), using several pulses for each hole.

For example, as demonstrated in Example 3 of the Examples section which follows, to perforate a PCL/PLA electrospun element (at a 3:1 ratio, respectively), 200 μm in total thickness, Eximer, KrF or XeF lasers can be used at an output power of about 200 watt, a rate of about 200 Hz and using 5 pulses for every hole.

It will be appreciated that such perforation can be used to enable the migration and/or proliferation of specific cell types through the electrospun element, and/or to enable the administration of various agents through the electrospun element.

Thus, the electrospun elements and scaffolds of the present invention can be used for ex vivo and/or in vivo formation of a tissue.

Thus, according to an additional aspect of the present invention there is provided a method of inducing ex vivo formation of a tissue. The method is effected by providing a scaffold having an electrospun element having a continuous gradient of average pore size along at least a portion thereof, a continuous porosity gradient, a continuous fiber weight per volume gradient, and/or a gradient of at least one agent; and (ii) seeding the scaffold with cells in a medium selected suitable for proliferation, differentiation and/or migration of the cells to thereby induce the formation of the tissue.

Preferably, the at least one agent used by the method according to this aspect of the present invention is for promoting cell colonization, differentiation, extravasation and/or migration. Such an agent can be a biological, chemical or mineral agent as described hereinabove.

The phrase "tissue" refers to part of an organism consisting of an aggregate of cells having a similar structure and function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue. Preferably, the phrase "tissue" as used herein also encompasses the phrase "organ" which refers to a fully differentiated structural and functional unit in an animal that is specialized for some particular function. Non-limiting examples of organs include head, brain, eye, bone (e.g., of leg and hand), heart, liver kidney, lung, pancreas, ovary, testis, and stomach. According to preferred embodiments of the present invention the tissue is a bone tissue.

The cells used by the method of this aspect of the present invention are capable of forming a tissue. Such cells can be for example, stem cells such as embryonic stem cells, bone marrow stem cells, cord blood cells, mesenchymal stem cells, adult tissue stem cells, or differentiated cells such as neural cells, retina cells, epidermal cells, hepatocytes, pancreatic cells, osseous cells, cartilaginous cells, elastic cells, fibrous cells, myocytes, myocardial cells, endothelial cells, smooth muscle cells, and hematopoietic cells.

As used herein the phrase "stem cell" refers to cells which are capable of differentiating into other cell types having a particular, specialized function (i.e., "fully differentiated" cells) or remaining in an undifferentiated state hereinafter "pluripotent stem cells".

Non-limiting examples of stem cells are hematopoietic stem cells obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation, and/or adult tissue stem cells [i.e., mesenchymal stem cells (MSCs)].

According to one embodiment of the present invention, the stem cells are bone marrow derived MSCs.

The term "seeding" refers to plating, placing and/or dropping the stem cells of the present invention into the scaffold of the present invention. It will be appreciated that the concentration of stem cells which are seeded on or within the scaffold of the present invention depends on the type of stem cells used and the composition of the electrospun element comprising the scaffold.

The medium used according to this aspect of the present invention can be any tissue culture medium supplemented with minerals and growth factors suitable for inducing the proliferation, differentiation and/or migration of the cells (e.g., stem cells) of the present invention into more specialized (i.e., differentiated) cells. For example, the osteogenic medium described in Example 1 of the Examples section which follows, was found capable of inducing the proliferation and differentiation of MSCs into osteoprogenitor cells capable of depositing a bone-like matrix onto the scaffold.

Following seeding the cells in the scaffold of the present invention the scaffolds are routinely examined using a microscope (e.g., an inverted microscope, an axioplan light microscope or an electronic microscope) for evaluation of cell growth, spreading and tissue formation (see for example FIGS. 1-3).

It will be appreciated that the ex vivo formed tissue can be further implanted in a subject in need thereof (e.g., a subject suffering from a pathology requiring tissue regeneration and/or repair as described hereinbelow). In such cases the cells seeded on the scaffold for ex vivo formation of a tissue can be derived from the treated individual (autologous source) or from allogeneic sources such as embryonic stem cells which are not expected to induce an immunogenic reaction.

Following ex vivo tissue formation the seeded scaffold is implanted in the subject. Those of skills in the art are capable of determining when and how to implant the scaffold to thereby induce tissue regeneration and treat the pathology. For example, if the pathology to be treated is a fractured bone the scaffold is seeded with MSCs or osteoblasts and following 14-21 days in culture the scaffold is preferably implanted in the damaged bone tissue.

The teachings of the method of the present invention can be also used to induce tissue formation in vivo and thus induce tissue regeneration and/or repair in a subject.

Thus, according to yet an additional aspect of the present invention, there is provided a method of inducing in vivo formation of a tissue. The method is effected by: (i) providing a scaffold having an electrospun element having a continuous gradient of average pore size along at least a portion thereof, a continuous porosity gradient, a continuous fiber weight-per-volume gradient, and/or a gradient of at least one and (ii) implanting the scaffold in a subject to thereby induce the formation of the tissue.

Thus, the scaffolds of the present invention can be used to induce tissue formation and/or regeneration and thus treat individuals suffering from tissue damage or loss.

Thus, according to another aspect of the present invention there is provided a method of treating a subject having a pathology characterized by a tissue damage or loss. The method is effected by: (i) providing a scaffold having a continuous gradient of average pore size along at least a portion thereof, a continuous porosity gradient, a continuous fiber weight-per-volume gradient, and/or a gradient of at least one agent and (ii) implanting the scaffold in a subject to thereby induce the formation of the tissue, thereby treating the subject.

As used herein the phrase "pathology characterized by tissue damage or loss" refers to any disorder, disease or condition exhibiting a tissue damage (i.e., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration. Examples for disorders or conditions requiring tissue regeneration include, but are not limited to, liver cirrhosis such as in hepatitis C patients (liver), Type-1 diabetes (pancreas), cystic fibrosis (lung, liver, pancreas), bone cancer (bone), burn and wound repair (skin), age related macular degeneration (retina), myocardial infarction, myocardial repair, CNS lesions (myelin), articular cartilage defects (chondrocytes), bladder degeneration, intestinal degeneration, and the like.

As used herein, the term "subject" includes both young and old human beings of both sexes. Preferably, this term encompasses individuals who suffer from pathologies as described hereinabove.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

Methods of implanting scaffolds in a subject are known in the art (Artzi Z, et al., 2005, J. Clin. Periodontol. 32: 193-9; Butler C E and Prieto V G, 2004, Plast. Reconstr. Surg. 114: 464-73).

According to another aspect of the present invention there is provided an article of manufacturing comprising an electrospun element having a continuous gradient of average pore size along at least a portion thereof, a continuous porosity gradient, a continuous fiber weight per volume gradient, and/or a gradient of at least one agent.

Preferably the at least one agent is a biological, chemical or mineral agent, preferably for promoting cell colonization, differentiation, extravasation and/or migration.

Any of the articles of manufacturing described hereinabove comprise a packaging material and the electrospun element of the present invention contained within the packaging material.

It is expected that during the life of this patent many relevant scaffolds will be developed and the scope of the term scaffold is intended to include all such new technologies a priori.

As used herein the term "about" refers to ±10%.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); "Absorbable and Biodegradable Polymers" Shalaby W. Shalaby, Karen J. L. Burg, Publisher: CRC Press, Boca Raton, Fla. (Oct. 27, 2003) ISBN: 0849314844; "Handbook of Biodegradable Polymers (Drug Targeting and Delivery)" A. J. Domb, Abraham J. Domb, Joseph Kost, David M. Wiseman, Publisher: T&F STM, London (Dec. 1, 1997) ISBN: 9057021536; "Synthetic Biodegradable Polymer Scaffolds (Tissue Engineering)" Anthony Atala, David J. Mooney, Publisher: Birkhauser Boston (Jan. 1, 1997) ISBN: 0817639195; all of which are incorporated by reference as if fully set forth herein. Other general references are provided throughout this document. The procedures therein are believed to be well known in the art and are provided for the convenience of the reader. All the information contained therein is incorporated herein by reference.

Example 1

PCL-PLA Electrospun Scaffolds are Highly Suitable for Guided Bone Regeneration

Materials and Experimental Methods
Electrospinning of Scaffolds—
Electrospun nanofibrous scaffolds were prepared from the following polymers: Poly(e-caprolactone) (PCL) with an average molecular weight of 80 kDa (Aldrich, USA) was dissolved in DMF (di-methyl formamide)/DCM(di-chloromethane) 25:75 to obtain 10% wt % solution.

Mixtures of PCL:PLA (3:1 ratio, respectively); PCL:PLA (9:1 ratio, respectively); PCL:PLA (1:3) and Acid hydrolyzed Collagen (1:3 ratio, respectively); PCL:Collagen hydrogel (1:9 ratio, respectively); PCL:PEO (3:1 ratio, respectively), and PCL:PEO (9:1 ratio, respectively). PLGA:PLA (1:1 ratio); PLGA:PCL:PLA (1:1:1 ratio). All numbers represent weight ratios between polymers.

Briefly, electrospinning was performed by delivering a polymer solution at a constant flow rate (0.5 ml/hour) through a plastic syringe with a capillary metal needle connected to a high voltage of several kilo volts (kV). A fluid jet was extruded from the capillary needle towards the grounded metal collector. As the jet accelerated towards the grounded metal collector, the solvent evaporated, and charged polymer fiber was deposited on a collector in the form of a nonwoven scaffold. The nonwoven scaffold was cut in round shapes to fit for example a single well of a 24-well plate (Nunc), sterilized and soaked with DMEM medium prior to cell seeding.

Collagen Based Hydrogel Scaffold—
To increase the strength of collagen hydrogels, the collagen containing solutions were crosslinked. Briefly, the copolymer PCL:Collagen acid hydrolyzed solution (Nitta Gelatin Co. Osaka, Japan-Producers of acid hydrolyzed collagen) was chemically crosslinked for about 30 minutes in the presence of 12.5 mM glutaraldehyde at 4° C. Following cross-linking, to block residual aldehyde groups of glutaraldehyde, the hydrogel solution was immersed for 1 hour in a 50 mM glycine aqueous solution at 37° C., rinsed with double distilled water (DDW), rinse twice with 100% ethanol and rinsed twice with PBS.

Composite scaffolds can be made using from hydrogel and electrospun elements. For example, the Acid hydrolyzed Collagen solution can be electrospun to produce a fiber matrix on which another Polymer solution (e.g., PCL-PLA) in another syringe can be electrospun. Following electrospinning, the electrospun element fibers can be soaked in water and the Acid hydrolyzed Collagen absorbs the water and forms a hydrogel. Alternatively, the Acid hydrolyzed Collagen can be prepared as a hydrogel (as described hereinabove), and the other polymer solution, e.g., PCL-PLA, can be electrospun on the top of the hydrogel.

Cell Source—
Human bone marrow derived mesenchymal stem cells (MSCs), human cord blood derived MSCs and rat bone marrow derived MSCs were used. Human cord blood MSCs were isolated using Ficoll gradient, human bone marrow MSCs were isolated from bone marrow aspirates and rat bone marrow MSCs were isolated from the femur of Sprague-Dawley rats (300-400 gram each rat) by flushing.

Culturing Conditions—
Cells (human or rat MSCs) were cultured up to three weeks in either a basal control medium [DMEM medium supplemented with 15% fetal calf serum (FCS), 20 mM L-glutamin, Pen-Strep (100 U/ml penicillin, 100 µg/ml streptomycin) or a basal control medium supplemented with 100 µg/ml ascorbic acid, 10 mM sodium β-glycerophosphate and $10^{-8}$ M dexamethasone ("the osteogenic medium", hereinafter). All culture medium and medium supplements were obtained from Biological Industries Beith Haemek, Israel and Sigma, USA.

The cells were cultured on the electrospun scaffold in 24-well plates (Nunc), 2,500,000 MSC cells per well, and samples were collected following one, two or three weeks for the various tests.

Histology and Immunohistochemistry for Bone Matrix Specific Markers—
The cultured cells were subjected to various morphology staining including Hematoxylin-Eosin and Masson's Trichrome staining. Selection of adherent osteoprogenitor cell subpopulation from MSCs was established by identifying the osteogenic cells using specific osteogenic cell markers including: osteocalcin immunoreactivity (bone matrix specific marker) (Biotest, USA), positive Alizarin red, von Kossa staining (reagents obtained from Sigma), and alkaline phosphatase activity [using a substrate α-naphtol phosphate (Sigma)].

Briefly, following their in vitro differentiation to osteoprogenitor cells, specimens of the electrospun scaffold were fixed for 60 minutes in Neutral buffered formalin (4% in 0.1 phosphate buffer, pH 7.2), following which the specimens were stained with Hematoxylin and eosin (H&E) for general morphology, with alizarin S, alkaline phosphatase and/or von kossa staining for synthesis of bone specific matrix and mineral deposition and with osoteocalcin for immunodetection of bone specific matrix formation.

Scanning Electron Micrograph (SEM) and Electron Dispersive Spectroscopy (EDS)—
were used for identification of mineral deposition indicated by the presence of Ca and Phosphate ions in the matrix.

Briefly, specimens of the scaffold and scaffold containing cells were fixed for 24 hours in 3% glutaraldehyde in 0.1 M Cacodylate buffer pH 7.2, dehydrated in graded ethanols, coated with gold palladium or carbon film and photographed by scanning electron microscope (SEM, 100 QT operating at 100 volts).

Experimental Results

Electrospun Scaffold are Nonwoven Networks with Randomly Oriented Fibers—

The electrospun scaffolds of the present invention (e.g., PCL:PLA at a 3:1 ratio, respectively) exhibited a 3-D structure of nonwoven, randomly oriented fibers with diameters ranging about 40-1000 nm. Large interconnected voids were present between the fibers forming a 3-D porous network. FIG. 1a illustrates an electrospun scaffold with fibers having an average diameter of 300 nm.

The PCL:PLA (3:1 Ratio, Respectively) Electrospun Scaffold is Capable of Supporting Differentiation of MSCs Towards the Bone Lineage—

Bone marrow-derived MSCs were cultured for 7 days on the PCL:PLA electrospun scaffold (at a 3:1 ratio, respectively) in the presence of the osteogenic medium revealed and a net-like arrangement of cell clusters (FIG. 1b). The amount of cell clusters increased gradually from two (FIG. 1c) to three (FIG. 1d) weeks in culture. As is further shown in FIGS. 1e-f, alizarin red S staining revealed the presence of mineralized bone matrix in the MSC-derived cultures, demonstrating bone regeneration. These cell clusters were also positive for osteocalcin staining which is indicative of synthesis of specific bone matrix (Not shown).

The PCL:PLA (at a 3:1 Ratio, Respectively) Electrospun Scaffold Supports Osteoprogenitor Cell Attachment to the 3-D Scaffold Porous Structure—

Scanning electron micrographs (SEM) of the PCL:PLA (at a 3:1 ratio, respectively) electrospun scaffold of the present invention revealed the scaffold 3-D porous structure (FIGS. 2a-b) and the attachment and mineral deposition by the MSCs derived osteoprogenitor cells following 7 days in culture (FIGS. 2c-d). Moreover, following 21 days in culture SEM analysis revealed large amount of extracellular matrix (ECM) deposits between the cells and fibers (FIGS. 3a-d). The amount of the ECM deposited increased gradually from 14 days (as seen by alizarin red S staining, FIG. 1e) to day 21 (FIG. 1f) and was shown to be mineralized (FIGS. 3a-d). The composition of the deposited mineralized matrix was further determined using Electron dispersive spectroscopy (EDS) and was found to be composed of Calcium and Phosphate ions at a ratio of 1.8 (not shown), similar to that observed in an intact bone.

These results demonstrate the capacity of the electrospun PCL:PLA (3:1 ratio, respectively) or other weight combination including also PLGA scaffold of the present invention to form a nonwoven, 3-D porous structured scaffold. In addition, the results presented here demonstrate the capacity of the electrospun scaffold of the present invention to support cell proliferation, attachment and differentiation towards osteogenic cells which transform the scaffold into a mineralized matrix. Thus, these results suggest the use of the PCL:PLA (3:1 ratio, respectively) or other weight combination including also PLA:PLGA (1:1 ratio) scaffold of the present invention in guided bone regeneration and/or repair.

Analysis and Discussion

The approaches for growing cells on scaffolds involve isolated bone marrow derived MSCs, recombinant signaling molecules, and three-dimensional (3-D) matrices. The main purpose of the scaffold is to provide the mechanical support needed to allow tissue regeneration while at the same time guiding cell-matrix and cell-cell interactions; morphology guides structure of engineered tissue, cell differentiation and function. The role of the scaffold is to allow the cells to attach, multiply, differentiate and transform from a nonspecific or primitive state into cells exhibiting the specific functions needed to support the MSCs. The ideal scaffold requirements include biocompatibility and biodegradability during replacement by cellular ECM components. Cord blood stem cells cultured on electrospun polymer 3-D scaffolds create a microenvironment for the differentiation of osteogenic progenitor cells. Electrospun PCL:PLA:PLGA: collagen hydrogel scaffolds combinations provide an optimal microenvironment for MSCs by simulation of the natural bone environment.

Results indicated that bone marrow-derived MSCs cultured in medium containing osteogenic supplements revealed the formation of cell clusters and mineral deposits. The amount of cell clusters and size increased gradually throughout culture. Characterization of cultured MSCs-derived osteoprogenitor cells was established by positive staining for Alizarin red S and positive osteocalcin immunohistochemistry.

This study tested the ability of electrospun biodegradable scaffold to provide a biocompatible 3-D environment for the establishment of osteoprogenitor cultures capable of supporting bone repair. The selection of osteogenic MSCs cultures were accomplished by supplementing them with specific osteogenic factors. Selected osteoprogenitor cells were identified by osteocalcin immunoreactivity, positive Alizarin red S, by von Kossa staining as well as by morphology and scanning electron microscopy (SEM) [Srouji and Livne 2005 (a)]. Results indicated that cord blood-derived MSCs cultured in medium containing osteogenic supplements revealed the formation of cell clusters and mineral deposits.

The 3-D scaffold produced by the electrospinning method was shown to accommodate MSCs in a high-density 3-D culture. Since the 3-D electrospun scaffold is manufactured at room temperature it can contain un-damaged biological additives such as growth factors, and other agents which support the implants against mechanical amortization and auto-immune phenomenon. The examined parameters include mechanical properties like fiber strength, morphology, the behavior of the implant in vitro for in vivo bone defect implanting.

One of the major challenges in the field of tissue engineering is the design of ideal scaffolds that mimic the tissue or structure. Bone repair is a process of reconstruction of the bone tissue in the area of injury. This process is regulated by number of systemic and local growth factors. Development of biodegradable electrospun scaffold combined with collagen hydrogel and or membrane scaffolds for the growth of MSCs will provide an ideal mechanical and biological environment for cell growth and development.

Results obtained from the study will contribute to clinical treatment by developing scaffold copolymer containing MSCs cells. This device will improve the carriers used today for implants and will contribute for better clinical use.

Another challenge for the scaffolding is to be reproducibly produced in a variety of shapes and compositions (chemically and morphologically) with minimal time and cost. The technique of electrospinning represents an exciting opportunity to meet these challenges by offering a simple approach to scaffold fabrication with controlled properties.

Example 2

Electrospun Elements with a Continuous or Step Wise Gradient of Porosity, Average Pore Size and/or Fiber Weight Per Volume The present inventors have uncovered a novel method for controlling the porosity, the average pore size and the average fiber weight per volume of electrospun elements, as follows.

Formation of Gradient Porosity, Average Pore Size and/or Weight Per Volume in Electrospun Elements—

Electrospinning is performed by delivering a polymer solution from a syringe with a capillary metal needle connected to a high voltage (several kV) towards a grounded wheel as a collecting electrode.

It will be appreciated that various parameters affect the porosity, average pore size, average fiber weight per volume, and/or fiber diameter. These include for example, the speed of the wheel to which the collecting electrode is connected, the flow rate of the polymer solution from the syringe, the concentration of the polymer solution in the dispensers (e.g., syringes), the voltage supplied to the polymer solution, the needle diameter, the distance between the syringe and the collecting vehicle (e.g., a drum or a wheel) and/or the temperature at which electrospinning occurs.

For example, changing the speed of the drum wheel to which the collecting electrode is connected affects the porosity and the average pore size. Thus, higher speed causes low porosity and low average pore size (see for example, FIG. 5) and lower speed causes high porosity and high average pore size (see for example, FIG. 4).

A gradient of fiber diameter can be achieved by using more than one syringe with variable polymer concentrations in each syringe. For example, a solution of 12% PCL/PLA in one syringe and a solution of 6% PCL/PLA in a second syringe. In addition, changing the flow rate proportion of the polymer solution from the syringe affects the proportion of fiber diameter. It will be appreciated that as a result, such an electrospun element comprises a gradient of weight per volume. Changing the voltage supplied to the polymer solution affects the fiber diameter and the polymer flow rate (and thus may also affect the gradient of weight per volume).

Changing the concentration of the polymer in the dispensers affects the fiber diameter. As is shown in FIGS. 6a-f, using PCL at the concentrations of 9, 10, 11, 13, 14 and 15% resulted in electrospun elements with fiber diameters ($\bar{d}_f$) of 0.4, 0.55, 0.6, 1, 1.1, and 1.5 µm, respectively.

Changing the concentration of the polymer affects the permeability of the electrospun element. Thus, as is further shown in FIGS. 6a-f, using PCL polymer solutions at the concentrations of 9, 10, 11, 13, 14 and 15% resulted in permeability values (as measured using a mercury porosimeter) of 0.24, 0.43, 0.6, 0.93, 1.39 and 1.82 darcy, respectively. It will be appreciated that such the permeability (measured in darcy units) reflects on the average pore size of the electrospun element.

Changing the needle diameter affects the fiber diameter. For example, using a voltage of 18 kV and a needle diameter of 270 µm can yield a constant flow rate of 0.1 ml/hour and a fiber diameter of 400 nm.

The distance between the syringe needle and the wheel rim can affect the porosity. For example, a polymer solution which is charged with 18 kV and flows at a rate of 0.1 ml/hour using a distance of 20 cm can result in an electrospun element with 85% porosity as opposed to an electrospun element in which the distance is 45 cm and which results in an electrospun element with 93% porosity. Thus, gradually changing the distance between the syringe needle and the wheel rim can result in a gradient of porosity.

An Example of a Formation of an Electrospun Element Having a Gradient Porosity—

A 5 ml syringe containing 10% PCL in DMC/DMF is positioned at a distance of 25 centimeters from the wheel rim. The polymer solution in the syringe is charged with 18 kV and the polymer solution flows from the syringe at an initial flow rate of 0.5 ml per hour. The initial speed of the wheel is 5 meter/minute (m/minute) and is changed gradually at intervals of 2 m/minute every 10 minutes to a final speed of 50 m/minute.

Example 3

Perforation of Electrospun Elements

The present inventors have uncovered experimental conditions suitable for perforating electrospun elements using electrical spark, laser beam and/or mechanical perforation.

An Example of Perforation of Electrospun Elements Using an Electrical Spark

An electrospun scaffold is made of PCL/PLA at a 3:1 ratio, respectively, as described in Example 1, hereinabove, with a total thickness of 200 µm. The electrospun scaffold can be perforated by passing an electrical spark through the electrospun element. This is performed by positioning the scaffold between an high voltage electrode (e.g., at 18 kV) and the ground electrode. The distance between the electrodes is about 10 mm. Electrical sparks produced between the high voltage electrode and the ground electrode results in holes through the scaffold.

An Example of Laser Perforation of Electrospun Elements

An electrospun scaffold is made of PCL/PLA at a 3:1 ratio, respectively, as described in Example 1, hereinabove, with a total thickness of 200 µm. The electrospun scaffold can be perforated using a laser. Suitable laser which can be used for perforating a scaffold can be for example, the Nd/Yag, Eximer, CO2, Dye and other laser capable of material processing. The perforation ability depends on the laser energy, power and wavelength.

For example, the Eximer laser can be used to perforate an electrospun element (e.g., PCL/PLA at a 3:1 ratio, respectively; total thickness of 200 µm) using output power of 200 watt, a rate of 200 Hz and using 5 pulses for every hole.

The KrF or XeF laser can be used to perforate an electrospun element (e.g., PCL/PLA at a 3:1 ratio, respectively; total thickness of 200 µm) using the following parameters: Energy: 200 Watt, rate: 200 Hz and using 5 pulses for every hole.

An Example of Mechanical Perforation of Electrospun Elements

An electrospun scaffold is made of PCL/PLA at a 3:1 ratio, respectively, as described in Example 1, hereinabove, with a total thickness of 200 µm. The electrospun scaffold can be perforated using a heated needle pillow (to about 100° C. in the case of PCL/PLA). The scaffold can be perforated by piercing, i.e., producing an array of holes.

Following perforation (using any of the perforation methods described hereinabove), the electrospun element (the scaffold) is immersed for 2 minutes in 0.1 N NaOH (for removal of fiber debris), washed 3 times with distilled water (for removal of NaOH remains), and dried at room temperature.

To prevent cell migration out through the perforated scaffold, a thin layer of electrospun scaffold, of about 20 µm, is weaved on either one or two sides of the perforated scaffold.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

Blumenfeld, I., Srouji, S., Lanir, Y., Laufer, D., Livne, E. 2002(a). Enhancement of bone defect healing in old rats by TGF-β and IGF-1. Exp. Gerontol. 37: 553-565.
Blumenfeld, I., Srouji, S., Peled, M., Livne, E. 2002(b). Metalloproteinases (MMP-2, -3) are involved in TGF-β and IGF-1—induced bone defect healing in old rats. Arch. Gerontol. Geriat. 35: 59-69.
D'Ippolito, G., Schiller, P. C., Ricordi, C., Roos, B. A., Howard. G. A., 1999. Age-related osteogenic potential of mesenchymal stromal cells from human vertebral bone marrow. J. Bone Min. Res. 14: 1115-1122.
Li W-J., Laurencin C. T., Caterson E. J., Tuan R. S., Ko F. K, 2002, Electrospun nanofibrous structure: A novel scaffold for tissue engineering. J. Biomed. Mater. Res. 60: 613-621.
Li W J, Danielson K G, Alexander P G, Tuan R S., 2003, Biological response of chondrocytes cultured in three-dimensional nanofibrous poly(epsilon-caprolactone) scaffolds. J. Biomed. Mater Res A. 67(4): 1105-14.
Li W.-J., Tuli R., Okafor C., Derfoul A., Danielson K., Hall D., Tuan R. S. 2005 A three-dimensional nanofibrous scaffold for cartilage tissue engineering using human mesemchymal stem cells. Biomaterials 26: 599-609.
Srouji, S., Livne, E., 2005(a), Bone marrow stem cells and biological scaffold for bone repair in aging and disease. Mech. Ageing. Dev. 126:281-287.
Srouji, S., Rachmiel, A., Livne. E., 2005(b), Mandibular defect repair by TGF-β and IGF-1 released from a biodegradable osteoconductive hydrogel. J. Craniomaxillofac Surg. 33(2): 79-84.
Tabata Y, Yamada K, Miyamoto S, Nagata I, Kikuchi H, Aoyama I, Tamura M, Ikada Y. Bone regeneration by basic fibroblast growth factor complexed with biodegradable hydrogels. Biomaterials. 1998; 19(7-9): 807-15.
Tabata Y, 2001. Recent progress in tissue engineering. Drug Discov Today. 6: 483-487.
Theron A, Zussman, E, Yarin A L, 2001, Electrostatic field-assisted alignment of electrospun nanofibers", Nanotechnology J., 12:3:384-390.
Tuli R, Nandi S, Li W J, Tuli S, Huang X, Manner P A, Laquerriere P, Noth U, Hall D J, Tuan R S. Human mesenchymal progenitor cell-based tissue engineering of a single-unit osteochondral construct. Tissue Eng. 2004, 10(7-8):1169-79.
Yamamoto, M., Tabata, Y., Ikada, Y. 1998. Ectopic bone formation induced by biodegradable hydrogels incorporating bone morphogenetic protein. J. Biomater. Sci. 9: 439-458.
Yoshimoto H., Shin Y. M., Terai H., Vacanti J. P. 2003; A biodegradable nanofiber scaffold by electrospinning and its potential for bone tissue engineering. Biomaterials 24: 2077-2082.

What is claimed is:

1. An article of manufacturing comprising an electrospun element having a continuous gradient of average pore size along at least a portion thereof, wherein said electrospun element comprises a single continuous fibrous filament.

2. The article of manufacturing of claim 1, wherein said electrospun element further has a continuous gradient of at least one agent along at least a portion thereof.

3. The article of manufacturing of claim 1, having a first surface and a second surface defining a volume therebetween, wherein said electrospun element has a continuous gradient of average pore size and a continuous gradient of at least one agent along at least a portion thereof, and wherein an average pore size close to said first surface is selected so as to allow migration of at least one population of cells therethrough into said volume, and an average pore size close to said second surface is selected so as to restrict migration of at least one population of cells therethrough into said volume.

4. The article of manufacturing of claim 1, wherein the article of manufacturing further comprises a culture medium for promoting proliferation of at least one population of cells being in contact with said electrospun element.

5. The article of manufacturing of claim 4, wherein said at least one population of cells are selected capable of guiding tissue regeneration.

6. The article of manufacturing of claim 4, wherein said at least one population of cells are osteoblast cells.

7. The article of manufacturing of claim 4, wherein said at least one population of cells are endothelial cells.

8. The article of manufacturing of claim 4, wherein said culture medium includes a mineralizing agent.

9. The article of manufacturing of claim 1, wherein said continuous gradient of average pore size is selected so as to allow migration of at least one population of cells through one side of said electrospun element.

10. The article of manufacturing of claim 9, wherein said continuous gradient of average pore size is selected so as to restrict migration of at least one population of cells through a second side, said second side opposite said first side, of said electrospun element.

11. The article of manufacturing of claim 10, wherein said at least one population of cells for which said migration is restricted are fibroblast cells.

12. The article of manufacturing of claim 1, wherein said continuous gradient of average pore size has a maximal average pore diameter of about 200 μm and a minimal average pore diameter of about 0.1 μm.

13. The article of manufacturing of claim 12, further comprising an electrospun element having a stepwise gradient of average pore size along at least a portion thereof.

14. The article of manufacturing of claim 1, wherein said electrospun element further exhibits a porosity gradient along at least a portion thereof.

15. The article of manufacturing of claim 14, wherein said porosity gradient is a continuous porosity gradient.

16. The article of manufacturing of claim 15, wherein said continuous porosity gradient has a maximal porosity of about 95% and a minimal porosity of about 50%.

17. The article of manufacturing of claim 14, wherein said porosity gradient is a stepwise porosity gradient.

18. The article of manufacturing of claim 1, wherein at least a portion of said single continuous fibrous filament is hollow.

19. The article of manufacturing of claim 1, wherein at least a portion of said single continuous fibrous filament comprises a core-shell structure.

20. The article of manufacturing of claim 1, wherein an average diameter of said single continuous fibrous filament is characterized by a variance of about 10%.

21. The article of manufacturing of claim 1, wherein said single continuous fibrous filament exhibits a gradient of average diameter along at least a portion of said electrospun element.

22. The article of manufacturing of claim 21, wherein said gradient of average diameter is a continuous gradient.

23. The article of manufacturing of claim 21, wherein said gradient of average diameter is a stepwise gradient.

24. The article of manufacturing of claim 1, wherein said electrospun element further has a gradient of weight-per-volume along at least a portion thereof.

25. The article of manufacturing of claim 1, wherein said electrospun element comprises at least one biocompatible polymer.

26. The article of manufacturing of claim 25, wherein said electrospun element comprises at least one biodegradable polymer.

27. The article of manufacturing of claim 1, wherein said electrospun element comprises a co-polymer.

28. The article of manufacturing of claim 27, wherein said co-polymer comprises at least one biocompatible polymer.

29. The article of manufacturing of claim 1, further comprising at least one agent.

30. The article of manufacturing of claim 1, wherein said electrospun element is perforated so as to allow selective migration of cells through said electrospun element.

31. The article of manufacturing of claim 1, wherein said electrospun element is comprised in a scaffold for in vivo formation of a tissue.

32. The article of manufacturing of claim 1, wherein said electrospun element consists of polycaprolactone (PCL) and polylactic acid (PLA) polymers and/or copolymers thereof.

33. An article of manufacturing comprising an electro spun element having a continuous gradient of average pore size along at least a portion thereof, wherein said electrospun element consists of a single continuous fibrous filament.

34. The article of manufacturing of claim 33, wherein said electrospun element further has a continuous gradient of at least one agent along at least a portion thereof.

35. The article of manufacturing of claim 33, having a first surface and a second surface defining a volume therebetween, wherein said electrospun element has a continuous gradient of average pore size and a continuous gradient of at least one agent along at least a portion thereof, and wherein an average pore size close to said first surface is selected so as to allow migration of at least one population of cells therethrough into said volume, and an average pore size close to said second surface is selected so as to restrict migration of at least one population of cells therethrough into said volume.

36. An article of manufacturing comprising a single electro spun element having a continuous gradient of average pore size along at least a portion thereof.

37. The article of manufacturing of claim 36, wherein said electrospun element further has a continuous gradient of at least one agent along at least a portion thereof.

38. The article of manufacturing of claim 36, having a first surface and a second surface defining a volume therebetween, wherein said electrospun element has a continuous gradient of average pore size and a continuous gradient of at least one agent along at least a portion thereof, and wherein an average pore size close to said first surface is selected so as to allow migration of at least one population of cells therethrough into said volume, and an average pore size close to said second surface is selected so as to restrict migration of at least one population of cells therethrough into said volume.

\* \* \* \* \*